United States Patent
Enger et al.

(10) Patent No.: US 8,608,977 B2
(45) Date of Patent: Dec. 17, 2013

(54) POLYMERIZABLE CHIRAL COMPOUNDS COMPRISING 2,6-NAPHTHYL AND ISOMANNITOL UNITS, AND USE THEREOF AS CHIRAL DOPANTS

(75) Inventors: Olivier Enger, Ludwigshafen (DE); Markus Hoffmann, Barcelona (ES); Jochen Brill, Speyer (DE); Stephan Maurer, Nuestadt-Gimmeldingen (DE); Bernd Ziegler, Goennheim (DE)

(73) Assignee: BASF SE, Ludwigshafen (DE)

( * ) Notice: Subject to any disclaimer, the term of this patent is extended or adjusted under 35 U.S.C. 154(b) by 141 days.

(21) Appl. No.: 12/996,543

(22) PCT Filed: Jun. 4, 2009

(86) PCT No.: PCT/EP2009/056857
§ 371 (c)(1),
(2), (4) Date: Dec. 6, 2010

(87) PCT Pub. No.: WO2009/153168
PCT Pub. Date: Dec. 23, 2009

(65) Prior Publication Data
US 2011/0092718 A1    Apr. 21, 2011

(30) Foreign Application Priority Data

Jun. 17, 2008   (EP) ..................... 08158439

(51) Int. Cl.
| | | |
|---|---|---|
| C09K 19/32 | (2006.01) |
| C09K 19/34 | (2006.01) |
| C09K 19/06 | (2006.01) |
| C09K 19/52 | (2006.01) |
| C09K 19/00 | (2006.01) |
| C07D 321/00 | (2006.01) |
| C07D 307/00 | (2006.01) |
| C07D 317/00 | (2006.01) |
| C07D 323/02 | (2006.01) |
| C07D 307/77 | (2006.01) |
| C07D 307/93 | (2006.01) |
| C07D 493/00 | (2006.01) |

(52) U.S. Cl.
USPC .......... 252/299.62; 252/299.01; 252/299.6; 252/299.61; 428/1.1; 549/200; 549/429; 549/456; 549/462; 549/464

(58) Field of Classification Search
USPC .......... 252/299.01, 299.6, 299.61, 299.62; 428/1.1; 549/200, 429, 456, 462, 464
See application file for complete search history.

(56) References Cited

U.S. PATENT DOCUMENTS

| | | |
|---|---|---|
| 5,050,966 A | 9/1991 | Berman |
| 5,235,443 A | 8/1993 | Barnik et al. |
| 5,506,704 A | 4/1996 | Broer et al. |
| 5,691,789 A | 11/1997 | Li et al. |
| 5,793,456 A | 8/1998 | Broer et al. |
| 5,948,831 A | 9/1999 | Broer et al. |
| 6,016,177 A | 1/2000 | Motomura et al. |

(Continued)

FOREIGN PATENT DOCUMENTS

| | | |
|---|---|---|
| DE | 198 35 730 | 2/1999 |
| DE | 198 43 724 | 4/1999 |

(Continued)

OTHER PUBLICATIONS

U.S. Appl. No. 13/090,800, filed Apr. 20, 2011, Brill, et al.

(Continued)

*Primary Examiner* — Geraldina Visconti
(74) *Attorney, Agent, or Firm* — Oblon, Spivak, McClelland, Maier & Neustadt, L.L.P.

(57) ABSTRACT

The present invention relates to compounds of the general formula I

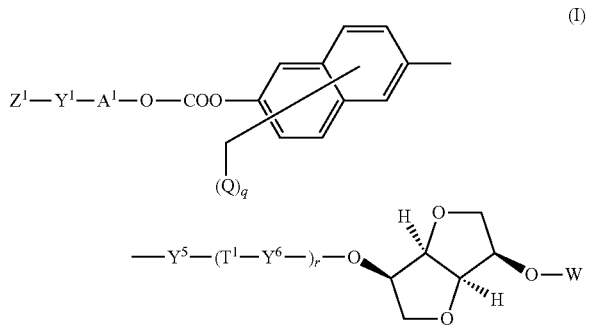

in which the variables are each defined as follows:
W is a $(Y^4\text{-}T^2\text{-})_s(Y^3\text{-}A^2\text{-})_tY^2\text{—}Z^2$ moiety,
$Z^1$, $Z^2$ are each independently unreactive radicals as defined more specifically in the description or reactive radicals through which polymerization can be brought about,
$A^1$, $A^2$ are each independently spacers as defined more specifically in the description,
$Y^1$ to $Y^5$ are linking units as defined more specifically in the description,
$Y^6$ is a chemical single bond or —CO—,
$T^1$, $T^2$ are each independently, as defined more specifically in the description, divalent saturated or unsaturated, optionally substituted and optionally fused iso- or heterocyclic radicals,
Q is substituents as defined more specifically in the description,
r, t are each independently 0 or 1,
s is 0, 1, 2 or 3
and
q is 0, 1, 2, 3 or 4.
The invention further relates to a liquid-crystalline composition which comprises at least one compound of the formula I, and to the use of the compounds of the formula I as chiral dopants.

13 Claims, No Drawings

(56) References Cited

U.S. PATENT DOCUMENTS

| | | | |
|---|---|---|---|
| 6,061,108 | A | 5/2000 | Anderson et al. |
| 6,099,758 | A | 8/2000 | Verrall et al. |
| 6,136,251 | A | 10/2000 | Etzbach et al. |
| 6,417,902 | B1 | 7/2002 | Greenfield et al. |
| 6,421,107 | B1 | 7/2002 | Greenfield et al. |
| 6,468,444 | B1 | 10/2002 | Meyer et al. |
| 2002/0013482 | A1 | 1/2002 | Brader et al. |
| 2007/0267599 | A1 | 11/2007 | Goldfinger et al. |
| 2011/0097562 | A1* | 4/2011 | Brill et al. .......... 428/212 |

FOREIGN PATENT DOCUMENTS

| | | |
|---|---|---|
| DE | 100 25 782 | 12/2001 |
| EP | 0 750 029 | 12/1996 |
| EP | 0 931 110 | 7/1999 |
| EP | 1 038 941 | 9/2000 |
| EP | 1 134 270 | 9/2001 |
| JP | 2002 179681 | 6/2002 |
| WO | 95 16007 | 6/1995 |
| WO | 95 22586 | 8/1995 |
| WO | 95 24454 | 9/1995 |
| WO | 95 24455 | 9/1995 |
| WO | 9602597 | 2/1996 |
| WO | 9604351 | 2/1996 |
| WO | 96 24647 | 8/1996 |
| WO | 97 00600 | 1/1997 |
| WO | 97 27251 | 7/1997 |
| WO | 97 27252 | 7/1997 |
| WO | 97 34862 | 9/1997 |
| WO | 98 47979 | 10/1998 |
| WO | 99 11733 | 3/1999 |
| WO | 99 19267 | 4/1999 |
| WO | 00 37585 | 6/2000 |
| WO | 00 47694 | 8/2000 |
| WO | 2006 120220 | 11/2006 |
| WO | 2007 120459 | 10/2007 |

OTHER PUBLICATIONS

Espinosa, M. A. et al., "New Cholesteric Liquid-Crystal Epoxy Resins Derived From 6-Hydroxy-2-Naphthoic Acid", Journal of Polymer Science: Part A: Polymer Chemistry, vol. 39, pp. 2847-2858, (Jun. 28, 2001).

International Search Report issued Sep. 25, 2009 in PCT/EP09/056857 filed Jun. 4, 2009.

U.S. Appl. No. 12/999,353, filed Dec. 16, 2010, Brill, et al.

* cited by examiner

POLYMERIZABLE CHIRAL COMPOUNDS COMPRISING 2,6-NAPHTHYL AND ISOMANNITOL UNITS, AND USE THEREOF AS CHIRAL DOPANTS

The present invention relates to compounds of the general formula I

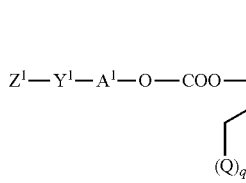 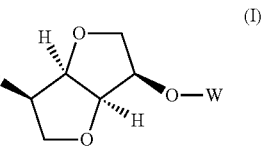

(I)

in which the variables are each defined as follows:

W is a $(Y^4\text{-}T^2\text{-})_s(Y^3\text{-}A^2\text{-})_t Y^2\text{-}Z^2$ moiety, $Z^1$, $Z^2$ are each independently hydrogen, optionally substituted $C_1$-$C_{20}$-alkyl in which the carbon chain may be interrupted by oxygen atoms in ether function, sulfur atoms in thioether function or by nonadjacent imino or $C_1$-$C_4$-alkylimino groups, or reactive radicals through which polymerization can be brought about, $A^1$, $A^2$ are each independently spacers which have from 1 to 30 carbon atoms and in which the carbon chain may be interrupted by oxygen atoms in ether function, sulfur atoms in thioether function or by nonadjacent imino or $C_1$-$C_4$-alkylimino groups, $Y^1$, $Y^2$ are each independently a chemical single bond, oxygen, sulfur, —CO—, —O—CO—, —CO—O—, —S—CO—, —CO—S—, —NR—CO— or —CO—NR—, $Y^3$ when s>0:
independently of $Y^1$ and $Y^2$ is as defined therefor or —O—COO—,
when s=0:
is a chemical single bond or —CO—, $Y^4$ is a chemical single bond, oxygen, sulfur, —CO—, —O—CO—, —CO—O—, —S—CO—, —CO—S—, —NR—CO— or —CO—NR—, with the proviso that $Y^4$, when bonded to the oxygen atom of the isomannitol unit, is a chemical single bond or —CO—, $Y^5$ when r=1:
is a chemical single bond, oxygen, sulfur, —CO—, —O—CO—, —CO—O—, —S—CO—, —CO—S—, —NR—CO— or —CO—NR—,
when r=0:
is a chemical single bond or —CO—, $Y^6$ is a chemical single bond or —CO—, R is hydrogen or $C_1$-$C_4$-alkyl, $T^1$, $T^2$ are each independently divalent saturated or unsaturated, optionally substituted and optionally fused iso- or heterocyclic radicals, Q is halogen, $NO_2$, NO, CN, CHO, $L^1$, CO-$L^1$, $X^1$—CO-$L^1$, $X^1$—SO-$L^1$, $X^1$—SO_2-$L^1$, $X^1$-$L^{1\prime}$, CO—$X^1$-$L^{1\prime}$, O—CO—$X^1$-$L^{1\prime}$, SO—$X^1$-$L^{1\prime}$ or $SO_2$—$X^1$-$L^{1\prime}$, where
$L^1$ is $C_1$-$C_{20}$-alkyl, $C_2$-$C_{20}$-alkenyl, $C_2$-$C_{20}$-alkynyl, $C_6$-$C_{10}$-aryl, heteroaryl having from 2 to 12 carbon atoms, $C_6$-$C_{10}$-aryl-$C_1$-$C_{20}$-alkyl, $C_6$-$C_{10}$-aryl-$C_2$-$C_{20}$-alkenyl, $C_6$-$C_{10}$-aryl-$C_2$-$C_{20}$-alkynyl, heteroaryl-$C_1$-$C_{20}$-alkyl, heteroaryl-$C_1$-$C_{20}$-alkenyl or heteroaryl-$C_1$-$C_{20}$-alkynyl having in each case from 2 to 12 carbon atoms in the heteroaryl radical, where the $C_1$-$C_{20}$ carbon chain may be interrupted by oxygen atoms in ether function, sulfur atoms in thioether function, nonadjacent imino, $C_1$-$C_{20}$-alkylimino and/or carbonyl groups, and both the $C_6$-$C_{10}$-aryl and the heteroaryl may be substituted by one or more substituents selected from the group consisting of halogen, $NO_2$, NO, CN, CHO, $L^2$, CO-$L^2$, $X^2$—CO-$L^2$, $X^2$—SO-$L^2$, $X^2$—SO_2-$L^2$, $X^2$-$L^{2\prime}$, CO—$X^2$-$L^{2\prime}$, O—CO—$X^2$-$L^{2\prime}$, SO—$X^2$-$L^{2\prime}$ and $SO_2$—$X^2$-$L^{2\prime}$, $L^{1\prime}$ is hydrogen or independently of $L^1$ is as defined for $L^1$, $L^2$ is $C_1$-$C_{20}$-alkyl, $C_2$-$C_{20}$-alkenyl, $C_2$-$C_{20}$-alkynyl, $C_6$-$C_{10}$-aryl, heteroaryl having from 2 to 12 carbon atoms, $C_6$-$C_{10}$-aryl-$C_1$-$C_{20}$-alkyl, $C_6$-$C_{10}$-aryl-$C_2$-$C_{20}$-alkenyl, $C_6$-$C_{10}$-aryl-$C_2$-$C_{20}$-alkynyl, heteroaryl-$C_1$-$C_{20}$-alkyl, heteroaryl-$C_2$-$C_{20}$-alkenyl or heteroaryl-$C_2$-$C_{20}$-alkynyl having in each case from 2 to 12 carbon atoms in the heteroaryl radical, $L^{2\prime}$ is hydrogen or independently of $L^2$ is as defined for $L^2$ and $X^1$, $X^2$ are each independently oxygen, sulfur or $NL^{1\prime}$ or $NL^{2\prime}$, r, t are each independently 0 or 1, s is 0, 1, 2 or 3,
where the particular variables $T^2$ and $Y^4$, in the case that s>1, may be the same as one another or different than one another, and q is 0, 1, 2, 3 or 4.

The invention further relates to a liquid-crystalline composition which comprises at least one inventive compound, and to the use of the inventive chiral compounds as dopants.

When heated, numerous compounds are not converted from the crystalline state with defined short-range and long-range order of the molecules directly into the liquid, unordered state, but rather pass through a liquid-crystalline phase in which the molecules are mobile but the molecule axes form an ordered structure. Elongated molecules often form nematic liquid-crystalline phases which are characterized by long-range orientation through parallel alignment of the longitudinal axes of the molecules. When such a nematic phase comprises chiral compounds or chiral molecular moieties, a chiral nematic or cholesteric phase can form, which is characterized by a helix like superstructure.

Owing to their remarkable optical properties, liquid-crystalline materials, especially nematic, chiral nematic or cholesteric materials, are of interest in applications including optical or electrooptical applications. Often, the temperature range within which the liquid-crystalline phase occurs is, however, outside the desired application temperature, or it extends only over a small temperature range. In addition, to establish chiral nematic phases, chiral compounds/dopants which have very good compatibility with the nematic host phase and bring about sufficiently great twisting, i.e. a sufficiently great "helical twisting power" ("HTP"), are required.

When the intention is to fix the liquid-crystalline ordered structures in the solid state, there are various possibilities. As well as glasslike solidification in the course of cooling from the liquid-crystalline state, there is the possibility of polymerization into polymeric networks or, in the case that liquid-crystalline compounds and if appropriate dopants comprise polymerizable groups, the polymerization of the liquid-crystalline compounds and if appropriate dopants themselves.

In addition, maximum birefringence of liquid-crystalline materials is often desirable. Considering this aspect, liquid-crystalline materials which comprise 2,6-naphthyl radicals in particular appear to possess a high potential. For such liquid-crystalline materials, however, suitable dopants must also be available, in order, in the desired case, for example, also to be able to establish chiral nematic phases with sufficient phase width.

Polymerizable dopants which comprise or may comprise isomannitol radicals are disclosed, for example, by documents WO 95/16007 A1, EP 0 750 029 A2 and DE 198 43 724 A1, but inventive compounds as described at the outset are neither mentioned nor suggested there.

It was thus an object of the present invention to provide further chiral compounds which have a comparatively high HTP, are suitable for the preparation of liquid-crystalline compositions and additionally form stable compositions in a wide mixing range of nematic host phase and chiral dopant and therefore do not have a tendency to demixing or phase separation.

Accordingly, the compounds of the formula I described at the outset have been found.

For the variables $Z^1$ and $Z^2$ in formula I, $C_1$-$C_{20}$-alkyl whose $C_1$-$C_{20}$ carbon chain may be interrupted by oxygen atoms in ether function may be, for example, methyl, ethyl, propyl, isopropyl, butyl, isobutyl, sec-butyl, tert-butyl, pentyl, isopentyl, neopentyl, tert-pentyl, hexyl, 2-methylpentyl, heptyl, hept-3-yl, octyl, 2-ethylhexyl, isooctyl, nonyl, isononyl, decyl, isodecyl, undecyl, dodecyl, tridecyl, 3,5,5,7-tetramethylnonyl, isotridecyl (the above terms isooctyl, isononyl, isodecyl and isotridecyl are trivial names and stem from the alcohols obtained by the oxo process—on this subject, cf. Ullmanns Encyklopädie der technischen Chemie, 4th edition, volume 7, pages 215 to 217, and also volume 11, pages 435 and 436), tetradecyl, pentadecyl, hexadecyl, heptadecyl, octadecyl, nonadecyl, eicosyl, methoxymethyl, 2-ethylhexoxymethyl, 2-methoxyethyl, 2-ethoxyethyl, 2-propoxyethyl, 2-isopropoxyethyl, 2-butoxyethyl, 2- or 3-methoxy-propyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 2- or 4-butoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 4,8-dioxadecyl, 3,6,8-trioxadecyl, 3,6,9-trioxaundecyl, 3,6,9,12-tetraoxamidecyl or 3,6,9,12-tetraoxatetradecyl; corresponding $C_1$-$C_{20}$-alkyl whose $C_1$-$C_{20}$ carbon chain may be interrupted by sulfur atoms in thioether function, nonadjacent imino, $C_1$-$C_{20}$-alkylimino and/or carbonyl groups can be derived formally from the oxygen-comprising radicals listed above by way of example by replacing the oxygen atoms with sulfur atoms, nonadjacent imino, $C_1$-$C_{20}$-alkylimino and/or carbonyl groups.

Suitable reactive radicals $Z^1$ and $Z^2$ by means of which polymerization can be brought about are, for example,

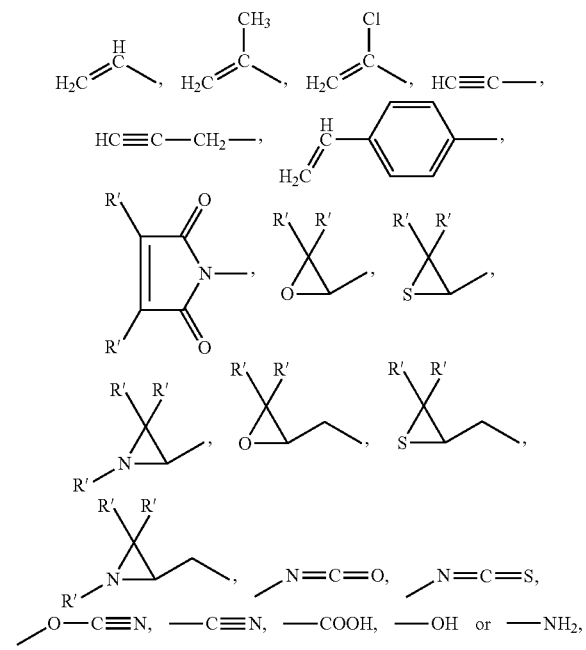

polymerization being understood to mean all reactions increasing the molecular weight of polymers, i.e. addition polymerizations as chain reactions, addition polymerization as staged reactions and condensation polymerizations.

The variables R' of the reactive radicals shown above by way of example are hydrogen or $C_1$-$C_4$-alkyl, i.e. methyl, ethyl, n-propyl, isopropyl, n-butyl, sec-butyl, isobutyl or tert-butyl, and may be the same or different.

Compounds having cyanate radicals may trimerize spontaneously to the corresponding cyanurates, and those having cyano radicals, especially with catalysis by acids, for example hydrochloric acid, or bases, to the corresponding triazines. Compounds having epoxide, thiirane, aziridine, isocyanate and isothiocyanate groups typically require further compounds with complementary reactive groups for polymerization. For example, isocyanates can polymerize with alcohols to give urethanes and with amines to give urea derivatives. The situation is similar for thiiranes and aziridines. The complementary reactive groups may be present in a second inventive compound which is mixed with the first, or they may be introduced into the polymerization mixture by auxiliary compounds which comprise two or more of these complementary groups. When these compounds comprise in each case two of these reactive groups, linear polymers having predominantly thermoplastic character are thus formed. When the compounds comprise more than two reactive groups, crosslinked polymers form which are mechanically particularly stable. The maleimido group is particularly suitable for free-radical copolymerization with olefinic compounds such as styrene.

Preferred reactive radicals $Z^1$ and $Z^2$ in the inventive compounds are selected from the group consisting of

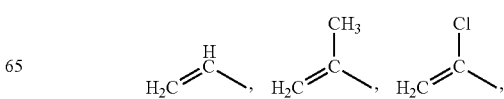

-continued

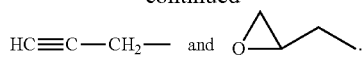

Particularly preferred reactive radicals Z¹ and Z² are

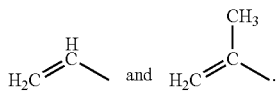

Preferred reactive moieties Z¹—Y¹ and Z²—Y² in the inventive compounds are selected from the group consisting of

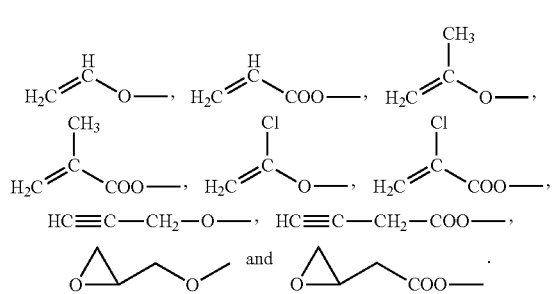

Particularly preferred reactive moieties Z¹—Y¹ and Z²—Y² in this context are

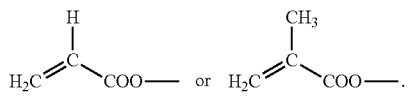

The variable R which appears in the bridges $Y^1$ to $Y^5$ is, in addition to hydrogen, also $C_1$-$C_4$-alkyl, i.e. methyl, ethyl, n-propyl, isopropyl, n-butyl, sec-butyl, isobutyl or tert-butyl.

Useful spacers $A^1$ and $A^2$ are all groups known for this purpose. The spacers comprise from 1 to 30, preferably from 3 to 12, carbon atoms and consist of predominantly linear aliphatic groups. They may be interrupted in the chain, for example, by nonadjacent oxygen or sulfur atoms or imino or $C_1$-$C_4$-alkylimino groups such as methylimino groups. Possible substituents for the spacer chain include fluorine, chlorine, bromine, cyano, methyl and ethyl.

Representative spacers $A^1$ and $A^2$ are, for example:

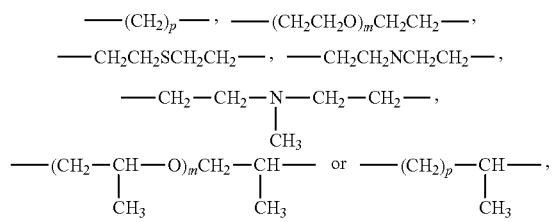

where m is from 1 to 3 and p is from 1 to 12.

The $T^1$ and $T^2$ radicals are divalent saturated or unsaturated, iso- or heterocyclic radicals. These may consist not only of one ring, but also of a plurality of rings fused to one another. For example, $T^1$ and $T^2$ also include divalent quinoline, decalin or naphthalene radicals.

Preferably, the $T^1$ and $T^2$ radicals in the compounds of the formula I are divalent radicals selected from the group consisting of

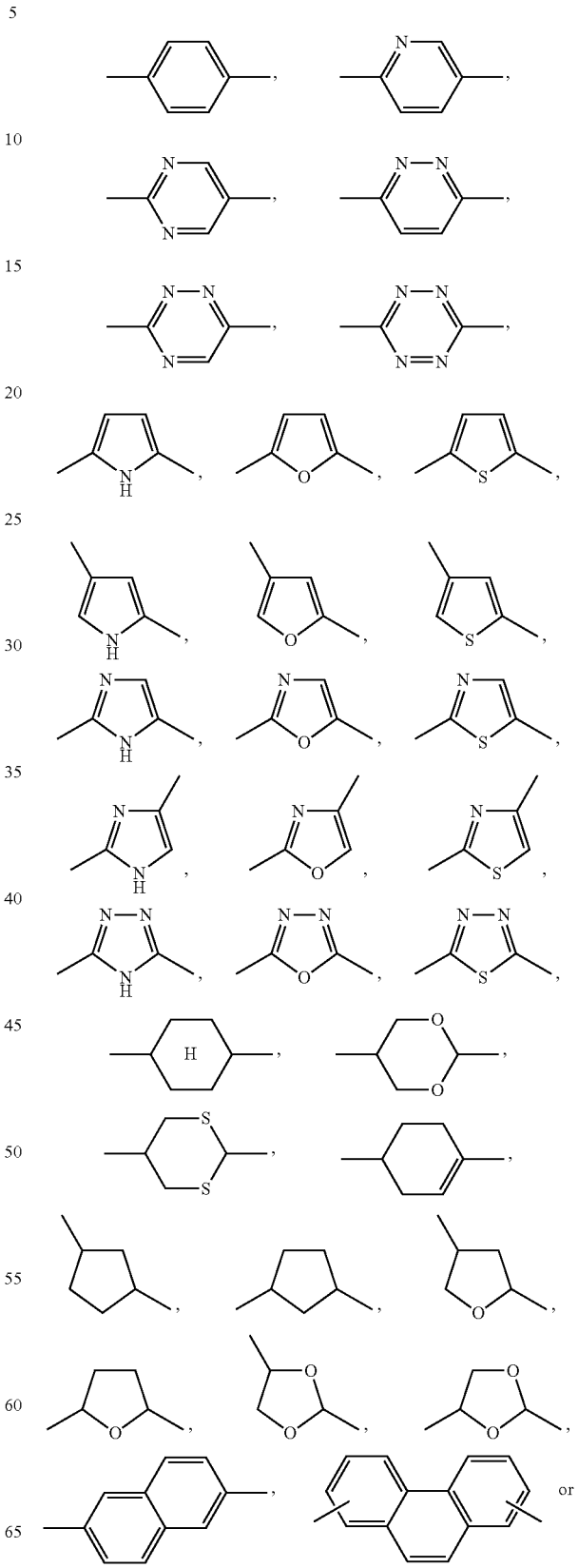

-continued

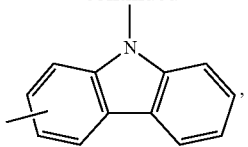

where the radicals

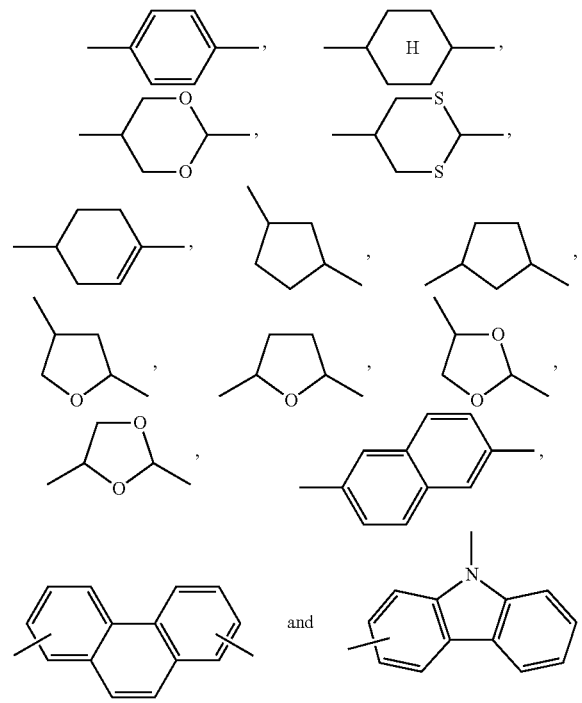

—irrespective of the specific selection of the Q substituents of the 2,6-naphthyl radical in formula I—may be substituted by up to four (q equal to 0, 1, 2, 3 or 4) identical or different Q substituents of the general definition already given above, the radical

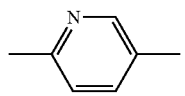

—irrespective of the specific selection of the Q substituents of the 2,6-naphthyl radical in formula I—may be substituted by up to three (q equal to 0, 1, 2 or 3) identical or different Q substituents of the general definition already given above, the radicals

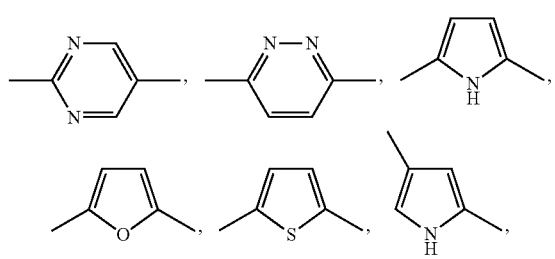

-continued

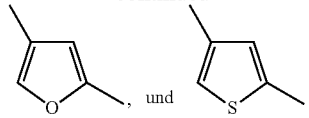

—irrespective of the specific selection of the Q substituents of the 2,6-naphthyl radical in formula I—may be substituted by up to two (q equal to 0, 1 or 2) identical or different Q substituents of the general definition already given above, and the radicals

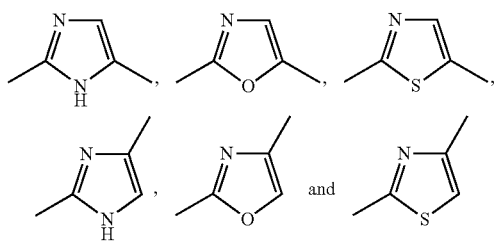

—irrespective of the specific selection of the Q substituents of the 2,6-naphthyl radical in formula I—may be substituted by up to one (q equal to 0 or 1) Q substituent of the general definition already given above.

In particular, the $T^1$ and $T^2$ radicals in the compounds of the formula I are divalent radicals selected from the group consisting of

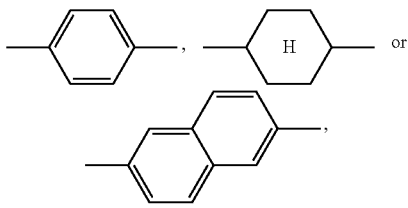

where the radicals—irrespective of the specific selection of the Q substituents of the 2,6-naphthyl radical in formula I—may be substituted by up to four (q equal to 0, 1, 2, 3 or 4) identical or different Q substituents of the general definition already given above.

Examples of the variables $L^1$ and $L^{1'}$ which occur in the definition of the variables Q when defined as $C_1$-$C_{20}$-alkyl whose $C_1$-$C_{20}$ carbon chain may be interrupted by oxygen atoms in ether function, sulfur atoms in thioether function, nonadjacent imino, $C_1$-$C_{20}$-alkylimino and/or carbonyl groups, and also of the variables $L^2$ and $L^{2'}$ when defined as $C_1$-$C_{20}$-alkyl, have already been listed by way of example above for the variables $Z^1$ and $Z^2$.

Examples of the variables $L^1$ and $L^{1'}$ which occur in the definition of the variables Q when defined as $C_2$-$C_{20}$-alkenyl whose $C_2$-$C_{20}$ carbon chain may be interrupted by oxygen atoms in ether function, sulfur atoms in thioether function, nonadjacent imino, $C_1$-$C_{20}$-alkylimino and/or carbonyl groups, and also of the variables $L^2$ and $L^{2'}$ when defined as $C_2$-$C_{20}$-alkenyl, are especially $C_2$-$C_{20}$-alk-1-enyl radicals. These radicals can be derived from suitable radicals listed above by way of example for the variables $Z^1$ and $Z^2$ by formal replacement of two hydrogen atoms which are located on adjacent carbon atoms by one further carbon-carbon bond.

Examples of the variables $L^1$ and $L^{1\prime}$ which occur in the definition of the variables Q when defined as $C_2$-$C_{20}$-alkynyl whose $C_2$-$C_{20}$ carbon chain may be interrupted by oxygen atoms in ether function, sulfur atoms in thioether function, nonadjacent imino, $C_1$-$C_{20}$-alkylimino and/or carbonyl groups, and also of the variables $L^2$ and $L^{2\prime}$ when defined as $C_2$-$C_{20}$-alkynyl, are especially $C_2$-$C_{20}$-alk-1-ynyl radicals. These radicals can be derived from suitable radicals listed above by way of example for the variables $Z^1$ and $Z^2$ by formal replacement of four hydrogen atoms which are located on adjacent carbon atoms by two further carbon-carbon bonds.

Examples of the variables $L^1$ and $L^{1\prime}$ which occur in the definition of the variables Q when defined as $C_6$-$C_{10}$-aryl-$C_1$-$C_{20}$-alkyl, $C_6$-$C_{10}$-aryl-$C_2$-$C_{20}$-alkenyl, $C_6$-$C_{10}$-aryl-$C_2$-$C_{20}$-alkynyl, heteroaryl-$C_1$-$C_{20}$-alkyl, heteroaryl-$C_2$-$C_{20}$-alkenyl and heteroaryl-$C_2$-$C_{20}$-alkynyl having in each case from 2 to 12 carbon atoms in the heteroaryl radical, where the $C_1$-$C_{20}$ carbon chain may be interrupted by oxygen atoms in ether function, sulfur atoms in thioether function, nonadjacent imino, $C_1$-$C_{20}$-alkylimino and/or carbonyl groups, and also of the variables $L^2$ and $L^{2\prime}$ in the definition of $C_6$-$C_{10}$-aryl-$C_1$-$C_{20}$-alkyl, $C_6$-$C_{10}$-aryl-$C_2$-$C_{20}$-alkenyl, $C_6$-$C_{10}$-aryl-$C_2$-$C_{20}$-alkynyl, heteroaryl-$C_1$-$C_{20}$-alkyl, heteroaryl-$C_2$-$C_{20}$-alkenyl and heteroaryl-$C_2$-$C_{20}$-alkynyl having in each case from 2 to 12 carbon atoms in the heteroaryl radical are especially those radicals which can be derived from the radicals listed above by way of example for the variables $Z^1$ and $Z^2$ by formal replacement of a terminal hydrogen atom by $C_6$-$C_{10}$-aryl or heteroaryl having from 2 to 12 carbon atoms.

For the variables $L_1$ and $L^{1\prime}$ and also $L^2$ and $L^{2\prime}$ which occur in the definition of the variables Q, $C_6$-$C_{10}$-aryl is especially phenyl and naphthyl.

For the variables $L^1$ and $L^{1\prime}$ and also $L^2$ and $L^{2\prime}$ which occur in the definition of the variables Q, heteroaryl having from 2 to 12 carbon atoms includes those radicals which derive, for example, from pyrrole, furan, thiophene, pyrazole, isoxazole, isothiazole, imidazole, 1H-1,2,3-triazole, 1H-1,2,4-triazole, pyridine, pyrazine, pyridazine, 1H-azepine, 2H-azepine, oxazole, thiazole, 1,2,3-, 1,2,4- or 1,3,4-oxadiazole, 1,2,3-, 1,2,4- or 1,3,4-thiadiazole, and also if appropriate the benzo- or dibenzofused rings, for example quinoline, isoquinoline, indole, benzo[b]furan (coumarone), benzo[b]thiophene (thionaphthene), carbazole, dibenzofuran, dibenzothiophene, 1H-indazole, indoxazole, benzo[d]isothiazole, anthranil, benzimidazole, benzoxazole, benzothiazole, quinoline, phthalazine, quinazoline, quinoxaline or phenazine.

In the case of the variables $L^1$ and $L^{1\prime}$ which occur in the definition of the variables Q, the $C_6$-$C_{10}$-aryl or heteroaryl having from 2 to 12 carbon atoms may be substituted by one or more substituents halogen, $NO_2$, NO, CN, CHO, $L^2$, CO-$L^2$, $X^2$—CO-$L^2$, $X^2$—SO-$L^2$, $X^2$—$SO_2$-$L^2$, $X^2$-$L^{2\prime}$, CO—$X^2$-$L^{2\prime}$, O—CO—$X^2$-$L^{2\prime}$, SO—$X^2$-$L^{2\prime}$ and $SO_2$—$X^2$-$L^{2\prime}$.

Halogen which occurs in the definition of the variables Q is fluorine, chlorine, bromine or iodine, especially fluorine or chlorine.

The variables $X^1$ and $X^2$ which occur in the definition of the variables Q are each independently oxygen, sulfur or $NL^{1\prime}$ or $NL^{2\prime}$.

Additionally preferred are those compounds in which $(Y^4$-$T^2$-$)_s$ in the variable W of the formula I corresponds to a moiety of the formula Ia

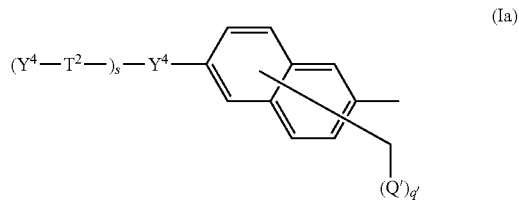

in which:

Q'—irrespective of the specific selection of the Q substituents of the 2,6-naphthyl radical in formula I—is identical or different Q substituents of the general definition already given above, q' is 0, 1, 2, 3 or 4 and s' is 0, 1 or 2, where the variables $Y^4$ and $T^2$ possess the same definition as already stated above and the variables $Y^4$ when s'>0 and the variables $T^2$ when s'>1 may be the same as one another or different than one another.

In these preferred compounds the variable W thus corresponds to the formula Ib shown below:

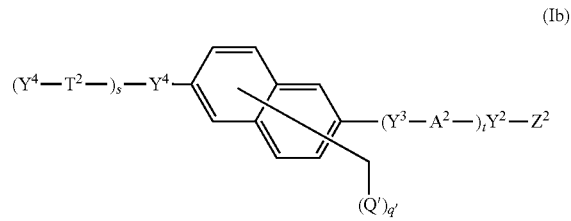

i.e. the preferred inventive compounds of this kind correspond to the formula Ic shown below:

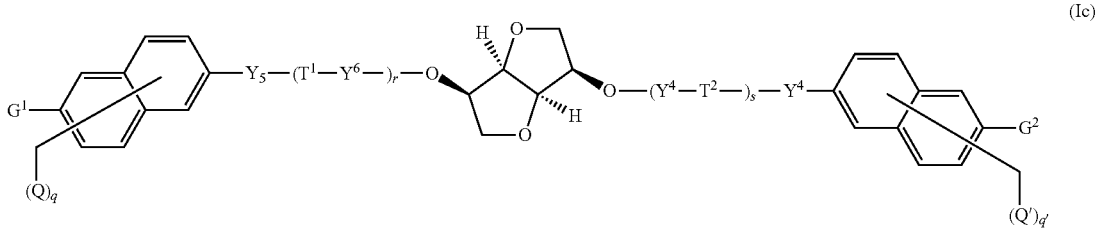

where $G^1$ and $G^2$ represent the $Z^1$—$Y^1$-$A^1$-O—COO— and $(Y^3$-$A^2$-$)_rY^2$—$Z^2$ moieties respectively.

Especially preferred are compounds of the formula I and of the formula Ic shown above, taking account of the above preferences, in which t assumes a value of 1 and $Y^3$ corresponds to an —O—COO— group.

Compounds of the formula Ic taking account of the above preference are:

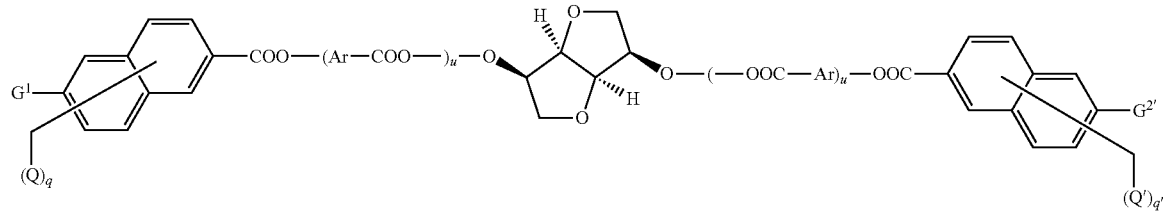

in which G1 and G2' are $Z^1$—$Y^1$-$A^1$-O—COO— and —OOC—O-$A^2$-$Y^2$—$Z^2$ moieties respectively, u and u' are each independently 0 or 1, Ar independently corresponds to a divalent 1,4-phenylene or divalent 2,6-naphthyl radical optionally substituted by Q substituents, and Q and Q' and q and q' are each as defined above.

Examples here include the compounds

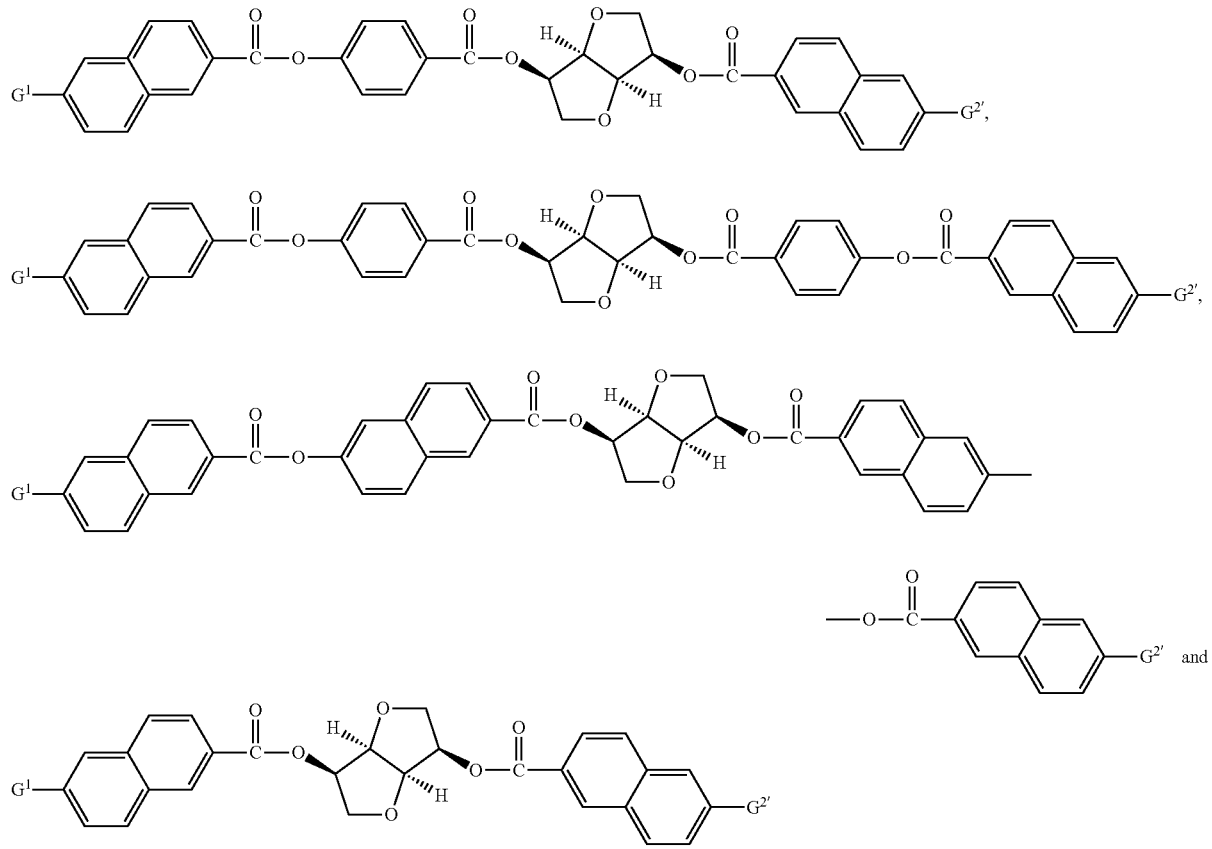

in which $G^1$ and $G^{2'}$ are $Z^1$—$Y^1$-$A^1$-O—COO— and —OOC—O-$A^2$-$Y^2$—$Z^2$ respectively.

In further preferred compounds, taking account of the above preferences, t assumes a value of 1 and the $Z^1$—$Y^1$-$A^1$- and -$A^2$-$Y^2$—$Z^2$ moieties are the same.

Especially preferred are those compounds of the formula I and Ic, taking account of the above preferences, in which at least one of the $Z^1$ and $Z^2$ radicals is a reactive radical.

Preference is given here, taking account of the above preferences, to those compounds in which at least one of the reactive $Z^1$ and $Z^2$ radicals is

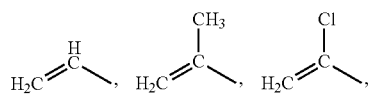

-continued

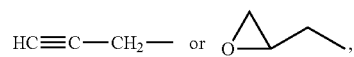

especially

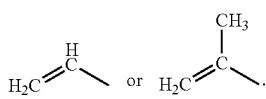

Additionally preferred, taking account of the above preferences, are those compounds in which $Z^1$—$Y^1$, and $Z^2$—$Y^2$ are identical reactive moieties

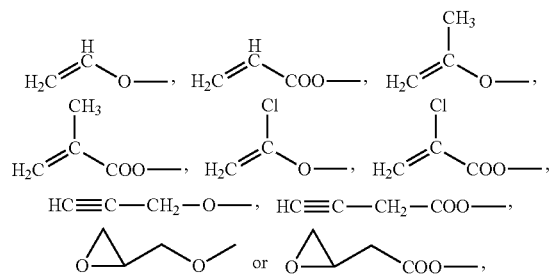

especially

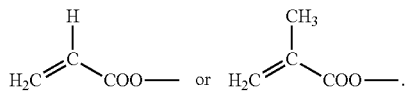

Taking account of the above preferences, particular mention is made here of the compounds in which $G^1$ and $G^{2'}$ are either
$H_2C$=CH—COO-$A^1$-O—COO— and —OOC—O-$A^2$-OOC—CH=$CH_2$ respectively or $H_2C$=C($CH_3$)—COO-$A^1$-O—COO— and —OOC—O-$A^2$-OOC—C($CH_3$)=$CH_2$ respectively.

The present invention further provides a liquid-crystalline composition which comprises at least one compound of the formula I and the above-described preferences.

The inventive liquid-crystalline composition may essentially be either nonpolymerizable or polymerizable.

A polymerizable or nonpolymerizable inventive liquid-crystalline composition should be understood quite generally not just to mean a composition whose one or more components already per se (in the temperature range of interest) have liquid-crystalline properties; instead, this should also be understood to mean a composition which only has liquid-crystalline behavior by virtue of mixing of the constituents or else only by addition of the inventive compounds (for example lyotropic systems). Moreover, the inventive compounds of the formula I and their preferred embodiments may already themselves have liquid-crystalline behavior, but need not necessarily possess this property.

A nonpolymerizable inventive composition is in particular a composition which is not capable of forming self-supporting polymerization or condensation products under customary polymerization conditions. This composition can be prepared, for example, by mixing suitable, commercially available liquid-crystalline materials, as find use, for example, for active LC layers in display technology, with one or more of the inventive compounds of the formula I or of their preferred embodiments. When the latter are compounds which comprise one or two reactive radicals $Z^1$ and $Z^2$, they are present in the inventive compositions in a concentration

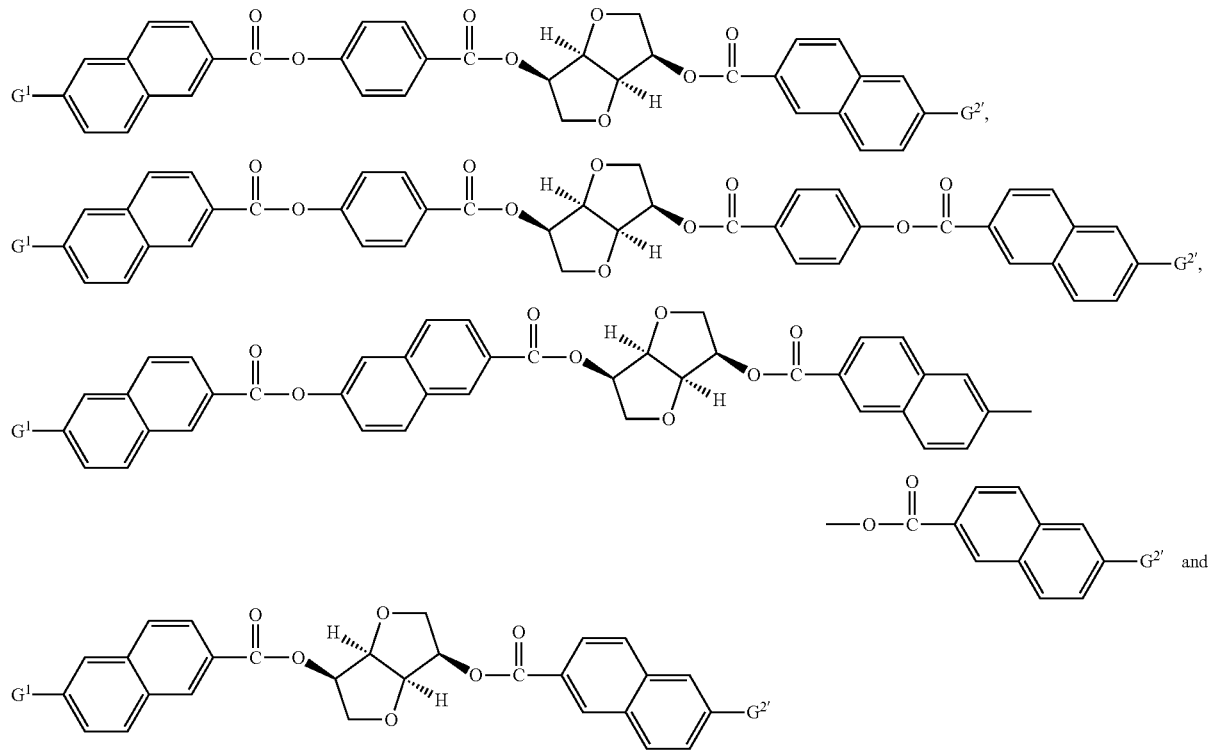

such as to be insufficient for generating correspondingly densely crosslinked self-supporting polymerization or condensation products.

A polymerizable inventive composition is in particular a composition in which at least one of the components is capable under customary polymerization conditions of forming polymerization or condensation products and which is polymerizable as such and can be polymerized or condensed to form self-supporting products.

Depending on the number of reactive radicals in the components of the polymerizable liquid-crystalline composition, the desired degree of polymerization, crosslinking and/or condensation on completion of polymerization or condensation can be established. This composition can be prepared readily by mixing suitable materials with one or more of the inventive compounds, these materials themselves being polymerizable or nonpolymerizable, liquid-crystalline or else non-liquid-crystalline.

Suitable polymerizable, liquid-crystalline materials are compounds which are described, for example, in the WO documents 95/22586 A1, 95/24454 A1, 95/24455 A1, 96/04351 A1, 96/24647 A1, 97/00600 A2, 97/34862 A1, 98/47979 A1 and 2006/120220 A1, and also the documents EP 1 134 270 A1 and DE 198 35 730 A1, and correspond substantially to the schematic structure P-Y-A-Y-M-Y-A-Y-P in which the variables P, Y and A are defined similarly to the variables $Z^1$ and $Z^2$, $Y^1$, $Y^2$, $Y^3$ and $A^1$ and $A^2$ in formula I, M denotes a mesogenic unit, and the linking Y group joined to the mesogenic M unit is specified by the —O—COO— group in formula I of the present application.

The reactive compounds which are listed in the document DE 100 25 782 A1 as constituent B) of the liquid-crystalline substance mixture described there may be added to the inventive liquid-crystalline composition as further monomers. These usually inexpensive compounds themselves generally do not exhibit liquid-crystalline behavior, but their addition opens up the possibility of reducing the proportion of expensive components in the inventive composition without noticeably influencing their liquid-crystalline behavior. In addition, it is possible with the aid of such reactive monomers to adjust, in a controlled manner, properties of the composition such as degree of crosslinking, viscosity, elasticity, etc. The selection of suitable reactive monomers can easily be accomplished by those skilled in the art, if appropriate after carrying out preliminary experiments. It should be noted here that such reactive compounds can also act as (auxiliary) compounds in the sense discussed above.

Mixing of nematic and inventive compounds affords a chiral nematic or cholesteric inventive composition which possesses particular optical properties, for instance color effects dependent on the viewing angle, reflection in the IR or UV wavelength range of the spectral region, etc.

The inventive liquid-crystalline compound may also comprise further additives. Useful such additives include photoinitiators, diluents, thickeners, defoamers and devolatilizers, lubricating and leveling assistants, thermal-curing or radiative-curing assistants, substrate wetting assistants, wetting and dispersing assistants, hydrophobizing agents, adhesion promoters and assistants for improving scratch resistance, dyes and pigments, and also additives selected from the group of the light, heat and/or oxidation stabilizers. The chemical and physical nature of these additives is addressed in detail in the documents WO 00/47694 A1.

By oligomerizing or polymerizing a polymerizable inventive liquid-crystalline composition, it is possible to prepare oligomers or polymers which may in particular also be obtained in the form of a film, i.e. of a self-supporting layer of uniform thickness. This film may be disposed on such a substrate that suitable measures make possible easy removal and transfer to another substrate for permanent disposition.

Such a film can be used, for example, in the field of film coating and in laminating processes.

Furthermore, such films, whose properties have been adapted to the particular end use, can be used in a wide variety of fields. For example, they may find use in devices for displaying visual information. Such devices are, for instance, video or overhead projectors, electrophoretic display devices, traffic displays, LCDs for use in computer monitors, televisions, visual display units in printers or kitchen appliances, and also advertising panels, illuminations and information panels, and additionally mobile visual display units, for example visual display units in cellphones, laptops, digital cameras, vehicles and destination displays on buses and trains. They may be present in these devices in a wide variety of functions, for example as color filters or films for the generation of wavelength-selective or broadband-polarized light.

It is additionally possible to coat or print substrates by means of the inventive polymerizable liquid-crystalline composition, by applying this composition to the substrate and subsequently polymerizing it.

With regard to the procedure for printing or coating substrates with liquid-crystalline materials, reference is made mutatis mutandis to the document WO 96/02597 A2. Furthermore, a polymerized layer which has been produced with the aid of such a procedure and partly or fully covers the original substrate surface should also be considered as a substrate, and so the production of multiply printed and/or coated substrates is also possible.

It should further be noted here that "printing" is typically understood to mean the incomplete coverage of the substrate surface, and "coating" to mean the full coverage of the substrate surface.

Useful substrates in addition to paper and card products, for example for carrier bags, magazines, brochures, gift packaging and packaging materials for consumer goods, consumable goods and luxury goods, are additionally also films, for instance for decorative and nondecorative packaging purposes, and also textiles of any type and leather. In addition, useful substrates are also those materials used to produce banknotes, securities, entrance tickets, and the like.

Further substrates are also goods for (entertainment) electronics, for example music cassettes (MCs), SVHS and VHS cassettes, minidisks (MDs), compact disks (CDs), digital versatile disks (DVDs) and the corresponding reproduction and/or recording units, televisions, radios, telephones/cellphones, computers, etc, and goods from the leisure, sports, domestic and games sector, for instance bicycles, children's vehicles, skis, snowboards and surfboards, inline skates, roller skates and ice skates and also domestic appliances. In addition, such substrates should also be understood to mean, for example, writing utensils and spectacle frames.

Further substrates are also a very wide variety of films which find use in optical or electrooptical components or in their production. Such films consist, for example, of polyvinyl alcohol (PVA), triacetylcellulose (TAC), polyimide (PI), polyvinyl cinnamate (PVC) or polyolefins, for instance polynorbornene, and may, for example, be (broadband) polarizers, light-guiding elements for background illumination in LCDs (known as "light guides"), films for the distribution of light (known as "BEFs", i.e. "brightness enhancement films") and films for the generation of polarized light in LCDs (known as "DBEFs", i.e. "dual brightness enhancement films"). Further substrates in this context may also be certain structural groups of the LCDs, for instance glass or polymer sheets which, if appropriate, also possess a transparent conductive coating, for example of indium tin oxide (ITO).

Light guides or BEFs can, for example, be produced by coating an appropriate substrate using an inventive polymerizable chiral nematic composition and subsequent polymerization thereof. The coating operation may be repeated more or less often with inventive compositions of the same or different composition in order to obtain corresponding optical components, for example retardation films, (broadband) polarizers and optical filters. This allows a correspondingly more compact structure of the optical components in LCDs to be produced.

The present invention further provides for the use of the inventive liquid-crystalline composition or of the inventive oligomer or polymer for producing optical components. Examples of these include LCDs and their components, for example (broadband) polarizers, optical filters, retardation films and BEFs.

With regard to the production of such components based on polymerizable liquid-crystalline materials, reference is made mutatis mutandis, for instance, to the document WO 00/37585 A1.

With regard to the use of an inventive polymerizable chiral nematic composition for producing (broadband) polarizers, reference is made mutatis mutandis, for example, to the documents U.S. Pat. Nos. 6,421,107, 6,417,902, 6,061,108, 6,099, 758, 6,016,177, 5,948,831, 5,793,456, 5,691,789 and 5,506, 704.

The inventive liquid-crystalline composition can also be used as a disperse liquid-crystalline phase in polymer dispersed liquid crystals (PDLCs). Such PDLCs may in principle either have an isotropic polymer matrix and both a macroscopic isotropic and anisotropic disperse liquid-crystalline phase, or an anisotropic polymer matrix and both a macroscopic isotropic and anisotropic dispersed liquid-crystalline phase, the macroscopic isotropic phase resulting from the random distribution of microscopic anisotropic domains.

In general, such PDLCs are produced starting from a (generally optically anisotropic) polymer film in which the liquid-crystalline phase is present uniformly dispersed in the form of ultrafine inclusions, typically in the micrometer or submicrometer size range. Stretching of the polymer film imposes anisotropic optical behavior both on the polymer matrix and on the dispersed phase. When inventive polymerizable liquid-crystalline compositions find use, the anisotropic state of the dispersed phase can be frozen by polymerization and hence, for example, significantly better thermal/thermal cycling stability can be achieved. The polymer matrix used here is usually polyvinyl alcohol.

In addition, an inventive polymerizable chiral nematic composition may, for example, also be used to prepare optical components, as described in the documents U.S. Pat. Nos. 5,235,443 and 5,050,966.

Further possible substrates are also surfaces to be encountered in the construction sector, such as building walls or else windowpanes. In the latter case, a functional effect may also be desired in addition to a decorative effect. Thus, it is possible to obtain multiple layers on the window material whose individual layers possess different chemical and physical properties. When, for example using an inventive chiral compound and a corresponding optical antipode, individual layers of polymerized liquid-crystalline compositions with opposite twist are applied, or, with addition of different concentrations of inventive chiral compound, individual layers of the polymerized liquid-crystalline composition of the same sense of rotation but in each case different pitch and hence different reflection properties are applied, it is possible in a controlled manner to reflect certain wavelengths or wavelength ranges of the light spectrum. In this way, an IR- or UV-reflective window coating, for example, is possible.

Thus, the polymerizable inventive liquid-crystalline composition or the oligomers or polymers which may be obtainable therefrom can be used to produce thermal insulation coatings which comprise one or more cholesteric layers which, in the infrared wavelength region, above 750 nm, in particular in the wavelength range from 751 nm to about 2000 nm, reflect at least 40%, in particular at least 45% of the incident radiation.

On this aspect of the polymerizable inventive liquid-crystalline composition, especially with regard to thermal insulation coatings, reference is made mutatis mutandis also to the document WO 99/19267 A1.

The inventive liquid-crystalline composition may additionally also find use as a liquid-crystalline colorant or for producing liquid-crystalline colorants. The use as colorant is possible when the composition is already colored per se. This color may be based on interference effects of the chiral nematic phase present and/or on absorption effects of dyes and/or pigments present. In addition, the composition, irrespective of whether it is colored or not, may also serve for the production of colorants. With regard to the preparation of liquid-crystalline colorants and their use for printing or coating substrates, reference is made mutatis mutandis to the document WO 96/02597 A2.

The inventive composition may additionally find use in the production of dispersions and emulsions which are preferably based on water. For the production of such dispersions and emulsions using liquid-crystalline materials, reference is made in this context to WO documents 96/02597 A2 and 98/47979 A1. These dispersions and emulsions may likewise be used for printing and coating substrates as have already been described above by way of example.

The inventive composition may further also find use in the production of pigments. The production of such pigments is known and is described, for example, comprehensively in the document WO 99/11733 A1. In addition, it is also possible to produce pigments preadjusted in shape and size using printing techniques or with the aid of networks in whose interstices the polymerizable composition is disposed. The subsequent polymerization or condensation of the liquid-crystal composition is followed in this case by the removal or leaching from the substrate or out of the network. These procedures are described in detail in the WO documents 96/02597 A1, 97/27251 A1, 97/27252 A1 and the document EP 0 931 110 A1.

These pigments can have a single layer or have a multilayered structure. The latter pigments are typically producible only when coating processes are employed in which a plurality of layers one on top of another is obtained successively and finally subjected to mechanical comminution.

For the above-described use of the inventive liquid-crystalline composition as a liquid-crystalline colorant or for preparing liquid-crystalline colorants, preference is given to making use of a polymerizable composition in the preparation of dispersions and emulsions and also in the preparation of pigments.

EXAMPLES

1) Synthesis Units

1.1) 6-(4-Acryloyloxybutoxycarbonyloxy)-2-naphthoic acid

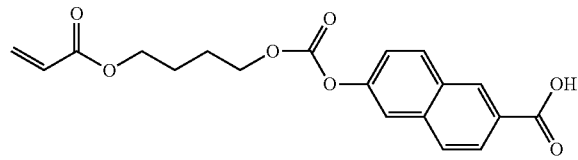 [SMILES: C=CC(=O)OCCCCOC(=O)Oc1ccc2cc(C(=O)O)ccc2c1]

was prepared according to WO 2006/120220 A1 (page 30, "A").

1.2) Preparation of Compound (1)

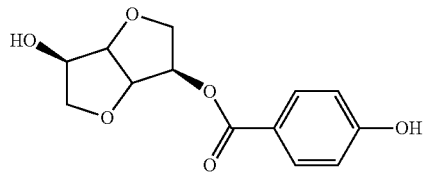

(1)

175.4 g (1.2 mol) of isomannitol and 138.1 g (1.0 mol) of 4-hydroxybenzoic acid were initially charged together with 8.2 g (0.04 mol) of p-toluenesulfonic acid monohydrate in 500 ml of xylene and heated to 140° C. The water of reaction which formed was separated out of this mixture. Subsequently, the xylene was removed from the reaction mixture by slow addition of 1 l of 1:1 water/methanol. This also separated out about 320 ml of water/methanol mixture. On completion of water separation, a further 1000 ml of water was added and the mixture was stirred at room temperature overnight. A brown solid precipitated out of the reaction solution, which comprised the compound (2) shown below as a by-product and was filtered off with suction. The desired product was present in the filtrate, which was concentrated and left to stand overnight. A yellowish solid precipitated out, which was filtered off, dissolved in hot water, filtered through silica gel and dried under reduced pressure at 60° C. overnight. 68.3 g of the above compound (1) were obtained.

1.3) Preparation of Compound (2)

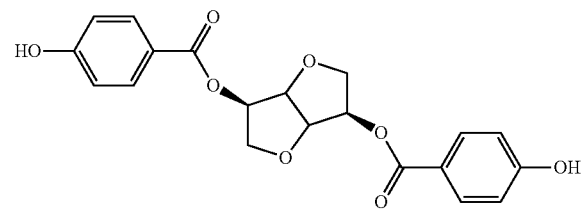

(2)

131.5 g (0.9 mol) of isomannitol and 273.5 g (1.98 mol) of 4-hydroxybenzoic acid were initially charged in 400 g of toluene and heated to 85° C. At this temperature, 3.9 g (0.039 mol) of 98% sulfuric acid were added. Subsequently, the mixture was heated further to reflux and the water of reaction which formed was separated out. After the water separation, 10.2 g of sodium carbonate, dissolved in 162 ml of water, were metered in and the mixture was stirred for a further 10 min. Thereafter, the solvent was exchanged for water by slow addition of 400 ml of hot water. On completion of exchange, beginning at 90° C., 400 ml of n-propanol were added. Thereafter, the mixture was cooled to room temperature. A sandy solid precipitated out of the reaction solution. This was filtered off with suction, washed with 300 ml of water and dried. 201.5 g (58%) of the above compound (2) were obtained.

1.4) Preparation of Compound (3)

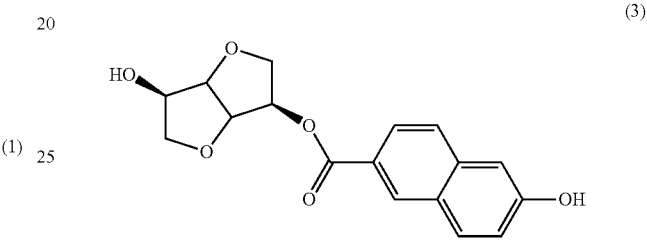

(3)

Compound (3) was prepared analogously to compound (1). Instead of 4-hydroxybenzoic acid, however, 6-hydroxy-2-naphthoic acid was used.

1.5) Preparation of Compound (4)

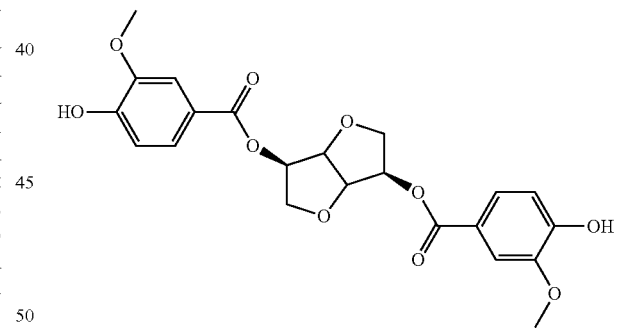

(4)

7.3 g (50 mmol) of isomannitol and 18.5 g (110 mmol) of 4-hydroxy-3-methoxybenzoic acid were initially charged in 90 g of toluene and heated to 100° C. At this temperature, 0.12 ml of conc. sulfuric acid was added. Subsequently, the mixture was heated further to reflux and the water of reaction which formed was separated out. After the water separation, 45 ml of methanol were metered in at 125° C. and the mixture was stirred for a further 10 min. Thereafter, 0.57 g of sodium carbonate, dissolved in 9.1 ml of water, was metered in and the mixture was stirred for a further 30 min. Thereafter, another 33 ml of methanol and 50 ml of water were added and the mixture was stirred for another 30 min. The reaction solution was heated again to 65° C. and filtered through silica gel. The filtrate was admixed with 4 g of activated carbon, boiled at reflux for one hour and hot-filtered. The filtrate was concentrated, precipitated with 200 ml of water and dried overnight. The product was filtered off with suction and, after drying overnight under reduced pressure, 5.7 g (26%) of the desired compound were obtained.

1.6) Preparation of Compound (5)

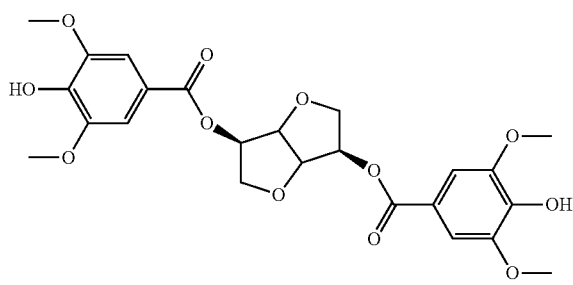

(5)

44.7 g (0.3 mol) of isomannitol and 130.8 g (0.66 mol) of 4-hydroxy-3,5-dimethoxybenzoic acid (syringic acid) were initially charged in 536.7 g of xylene and heated to 100° C. At this temperature, 0.73 ml of conc. sulfuric acid was added. Subsequently, the mixture was heated to reflux further and the water of reaction which formed was separated out. After the water separation, 271.5 ml of methanol were metered in at 125° C. and the mixture was stirred for a further 10 min. Thereafter, 3.4 g of sodium carbonate, dissolved in 54.3 ml of water, were metered in and the mixture was stirred for a further 30 min. Subsequently, 149.3 g of methanol and 299 ml of water were added and the mixture was stirred for another 30 min. The mixture then left to stand overnight at room temperature. Product precipitated out. This was filtered off with suction. The material filtered off was dissolved at 65° C. in 1000 ml of methanol and filtered through silica gel. The filtrate was mixed with 4 g of activated carbon, boiled at reflux for two hours and hot-filtered. Solid precipitated out of the filtrate. This was filtered off with suction and, after drying under reduced pressure, 54.5 g (36%) of the desired compound were obtained.

1.7) Preparation of Compound (6)

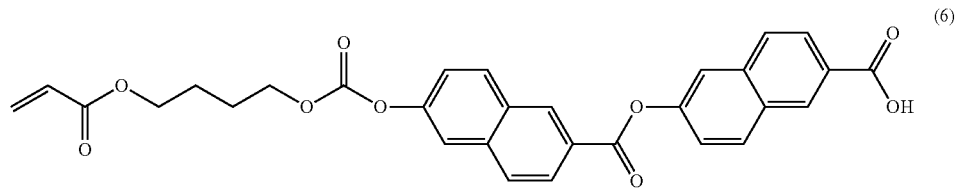 [SMILES: C=CC(=O)OCCCCOC(=O)Oc1ccc2cc(C(=O)Oc3ccc4cc(C(=O)O)ccc4c3)ccc2c1]

(6)

7.4 g (20 mmol) of 6-(4-acryloyloxybutoxycarbonyloxy)-2-naphthoic acid were stirred in 30 ml of oxalyl chloride with addition of 7 mg of Kerobit BHT and 4 drops of DMF for one hour. Subsequently, the excess oxalyl chloride was distilled off. The residue was dissolved in 40 ml of ethylene glycol dimethyl ether and added dropwise at 0-5° C. to a solution consisting of 37.6 g (200 mmol) of 6-hydroxy-2-naphthoic acid, 8.6 g (66 mmol) of N,N-dimethylcyclohexylamine and 250 ml of N,N-dimethylacetamide. The mixture was stirred at 0-5° C. for a further hour and at room temperature over the weekend. The mixture was then precipitated in 1 l of water. The resulting precipitate was stirred in 250 ml of methanol, filtered off with suction and dried. 6.7 g (62%) of the desired compound were obtained.

2) Inventive Compounds

HTP values were determined by Cano's method on mixtures of the inventive compounds with the nematic compound of the hereinbelow indicated formula:

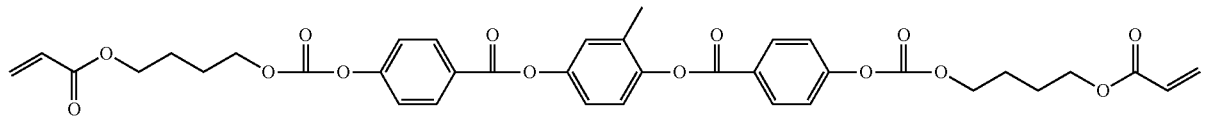 [SMILES: C=CC(=O)OCCCCOC(=O)Oc1ccc(C(=O)Oc2ccc(OC(=O)c3ccc(OC(=O)OCCCCOC(=O)C=C)cc3)c(C)c2)cc1]

(preparation see WO 97/00600 A2, pages 29/30, example 6).

2.1) Preparation of the Compound

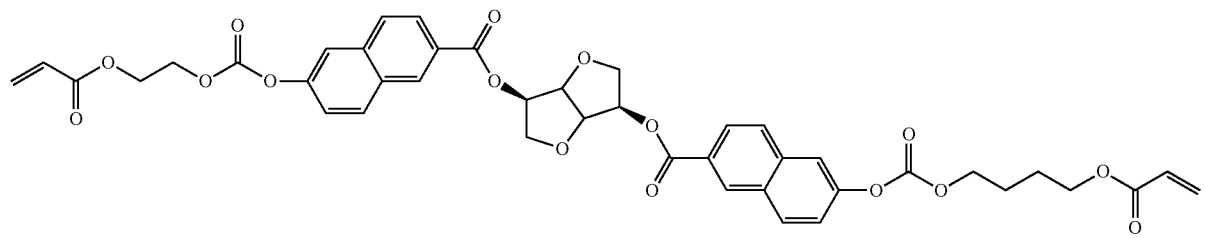 [SMILES: C=CC(=O)OCCCCOC(=O)Oc1ccc2cc(C(=O)O[C@@H]3COC4C3OC[C@H]4OC(=O)c3ccc4cc(OC(=O)OCCOC(=O)C=C)ccc4c3)ccc2c1]

12.2 g (33 mmol) of 6-(4-acryloyloxybutoxycarbonyloxy)-2-naphthoic acid were stirred in 75 ml of oxalyl chloride with addition of 10 mg of Kerobit BHT and 5 drops of DMF for one hour. Subsequently, the excess oxalyl chloride was distilled off. The residue was dissolved in 65 ml of ethylene glycol dimethyl ether and added dropwise at 0-5° C. to a solution consisting of 2.2 g (15 mmol) of isomannitol, 9.0 g (71 mmol) of N,N-dimethylcyclohexylamine and 50 ml of N,N-dimethylacetamide, and then stirred at 0-5° C. for a further 30 min. The reaction mixture was then stirred at 40° C. for 3 hours. The mixture cooled to room temperature overnight. The next morning, the mixture was precipitated in 400 g of ice/water and 15 ml of conc. hydrochloric acid, stirred for 3 hours and then filtered with suction. The resulting material filtered off was stirred in 400 ml of methanol, stirred for a further 4 hours and then purified by means of column chromatography (SiO₂, 1:1 petroleum ether/ethyl acetate). 0.9 g (<10%) of the desired compound was obtained.

2.2) Preparation of the Compound 21.0 g (57 mmol) of 6-(4-acryloyloxybutoxycarbonyloxy)-2-naphthoic acid and 21 mg of 4-methoxyphenol were initially charged in 31.5 mg of ethylene glycol dimethyl ether and dissolved at 45° C. Then 0.14 g of DMF was added and 7.6 g (59 mmol) of oxalyl chloride were added dropwise at a maximum temperature of 50° C. After a continued stirring time of 2 hours at 45-50° C., the acid chloride prepared was added dropwise at 0-2° C. to a solution consisting of 9.7 g (25 mmol) of the compound (2), 2 mg of 4-hydroxy-2,2,6,6-tetramethylpiperidine 1-oxyl (hydroxy-TEMPO) and 15.2 g (119 mmol) of N,N-dimethylcyclohexylamine in 31.5 g of N,N-dimethylacetamide. The mixture was stirred at 0° C. for a further hour, then heated to 40° C. and stirred at this temperature for three hours. After cooling to room temperature, 11.8 ml (74 mmol) of 20% hydrochloric acid and 150 ml of methanol were added and the mixture was stirred for a further 4 hours. The precipitated product was filtered off with suction, washed with 100 ml of water and dried. 24.5 g (92%) of the desired product were obtained.

HTP=34 μm⁻¹

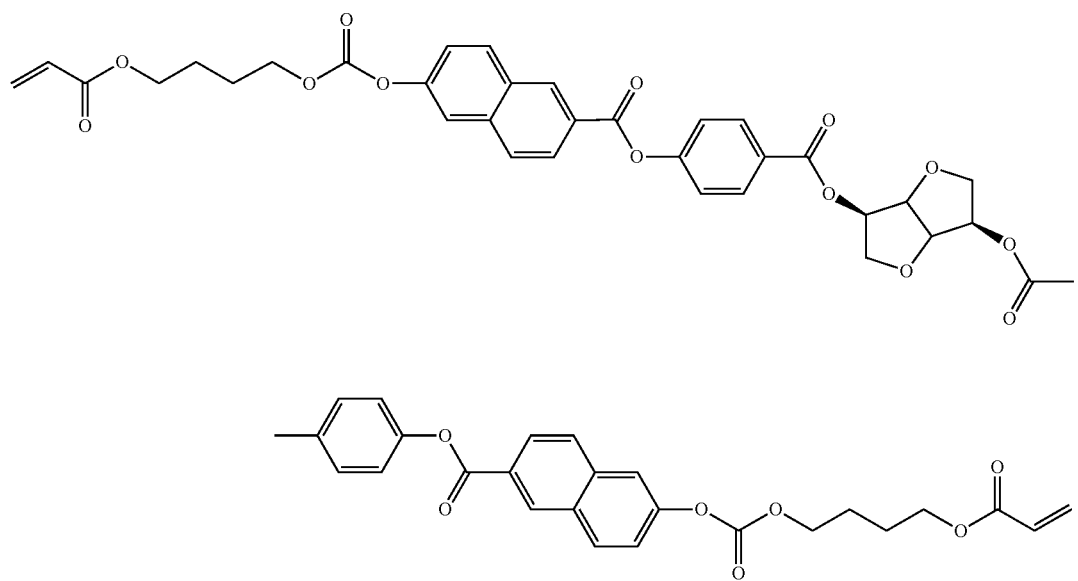

2.3) Preparation of a Mixture of the Compounds

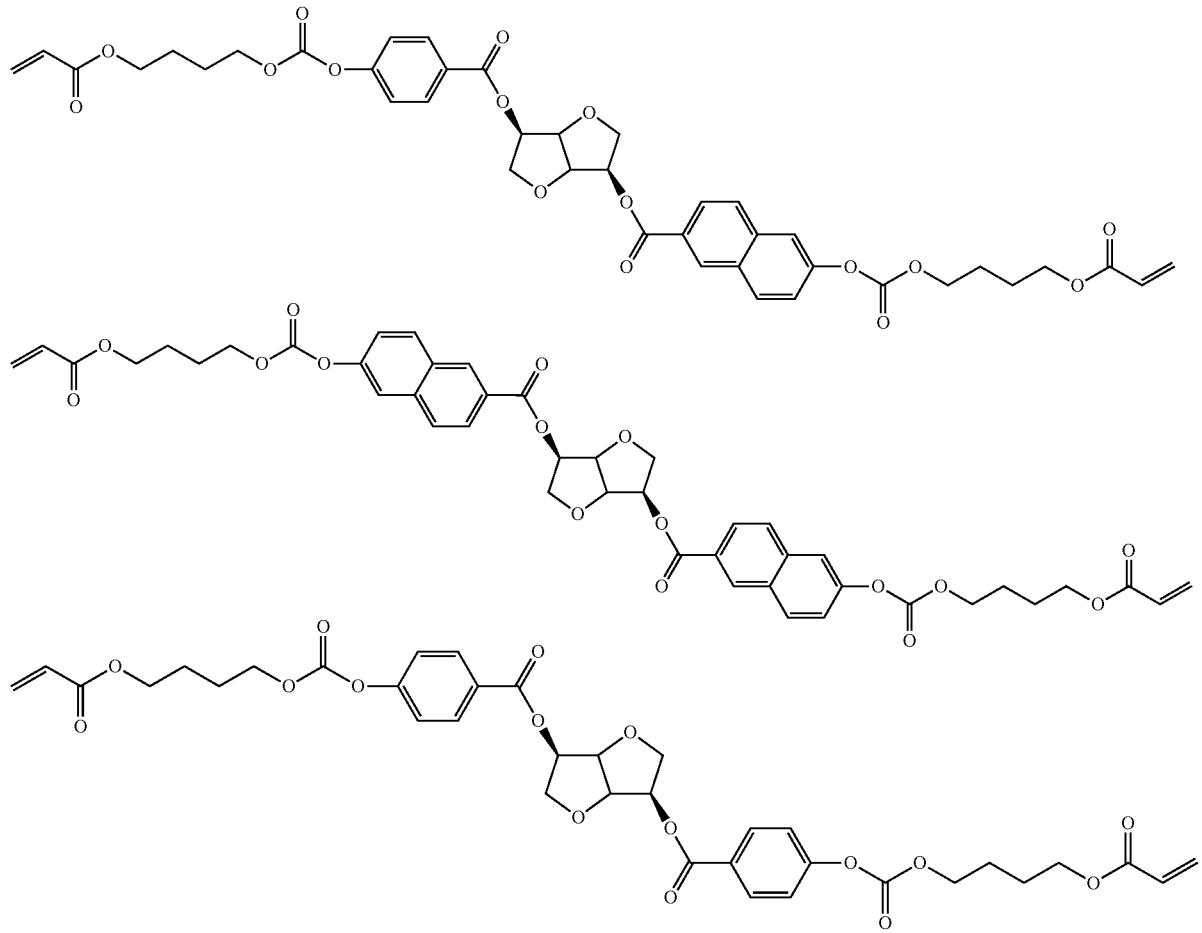

A mixture of 13.8 g (37 mmol) of 6-(4-acryloyloxybutoxy-carbonyloxy)-2-naphthoic acid and 11.8 g (37 mmol) of 4-(4-acryloyloxybutyloxycarbonyloxy)benzoic acid (prepared according to WO 97/00600 A2) was stirred in 160 ml of oxalyl chloride with addition of 24 mg of Kerobit BHT and 11 drops of DMF for one hour. Subsequently, the excess oxalyl chloride was distilled off. The residue was dissolved in 100 ml of methylene chloride and added dropwise at 0-5° C. to a solution consisting of 4.7 g (32 mmol) of isomannitol, 19 g (150 mmol) of N,N-dimethylcyclohexylamine and 100 ml of methylene chloride. The mixture was stirred at 0-5° C. for 30 min and at room temperature overnight. Then the reaction mixture was stirred at 40° C. for 5 hours. After cooling to room temperature, the solution was washed first with acidic water (pH 3) and then with water. The organic phase was dried over sodium sulfate and partly concentrated. The remaining concentrated solution was filtered with 100 ml of methanol and stirred overnight. The resulting product was filtered off with suction, then stirred again in 150 ml of 1:1 methanol/water and then filtered. The material filtered off was dissolved in 100 ml of methylene chloride, admixed with 10 g of silica gel and, after briefly stirring, filtered. The filtrate was concentrated by half, precipitated with 150 ml of n-hexane and stirred overnight. The product was filtered off with suction and dried under reduced pressure at 40° C. overnight. 3.4 g (14%) of the desired compounds were obtained.

2.4) Preparation of the Compound

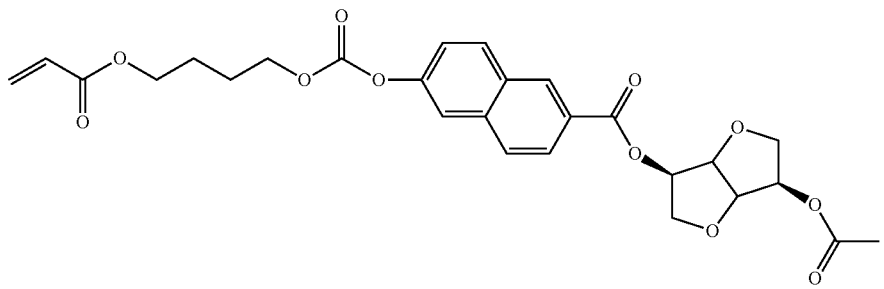

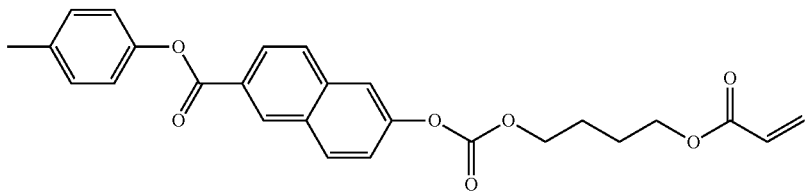

17.0 g (46 mmol) of 6-(4-acryloyloxybutoxycarbonyloxy)-2-naphthoic acid were stirred in 65 ml of oxalyl chloride with addition of 15 mg of hydroxy-TEMPO and 9 drops of DMF for one hour. Subsequently, the excess oxalyl chloride was distilled off. The residue was dissolved in 90 ml of methylene chloride and added dropwise at 0-5° C. to a solution consisting of 5.3 g (20 mmol) of the compound (1), 11.7 g (90 mmol) of N,N-dimethylcyclohexylamine and 90 ml of methylene chloride. The mixture was stirred at 0-5° C. for 30 min and at room temperature overnight. The reaction mixture was then stirred at 40° C. for 6.5 hours. After cooling to room temperature, the solution was washed first with 200 ml of acidic water (pH 3) and then with 200 ml of water. The organic phase was dried over sodium sulfate and filtered. The filtrate crystallized as a result of addition of 300 ml of methanol. The mixture was stirred overnight and filtered with suction the next morning. For purification, the material filtered off was dissolved in methylene chloride, filtered through silica gel and then concentrated. The remaining residue was admixed with a little n-hexane, precipitated with methanol and stirred overnight. The resulting product was filtered off with suction and dried at 40° C. under reduced pressure overnight. 0.7 g (4%) of the desired compound was obtained.

HTP=35 μm$^{-1}$ 2.5) Preparation of the Compound

The synthesis was effected in two stages:

Stage 1:

4.8 g (15 mmol) of 4(4-acryloyloxybutyloxycarbonyloxy) benzoic acid were stirred in 35 ml of oxalyl chloride with addition of 5 mg of hydroxy-TEMPO and 3 drops of DMF for one hour. Subsequently, the excess oxalyl chloride was distilled off. The residue was dissolved in 45 ml of methylene chloride and added dropwise at 0-5° C. to a solution consisting of 4.4 g (17 mmol) of compound (1), 6.4 g (50 mmol) of N,N-dimethylcyclohexylamine and 45 ml of methylene chloride, and then the mixture was stirred at 0-5° C. for 1.5 hours. The mixture was washed first with 125 ml of slightly acidic water (pH 5) and then with 125 ml of water. The organic phase was dried over sodium sulfate and filtered through silica gel. The filtrate was transferred to a flask and cooled again to 0-5° C.

Stage 2:

7.4 g (20 mmol) of 6-(4-acryloyloxybutoxycarbonyloxy)-2-naphthoic acid were stirred in 30 ml of oxalyl chloride with addition of 7 mg of hydroxy-TEMPO and 4 drops of DMF for one hour. Subsequently, the excess oxalyl chloride was distilled off. The residue was dissolved in 40 ml of methylene chloride and added dropwise at 0-5° C. to the already prepared filtrate from stage 1, admixed with 9.0 g (70 mmol) of N,N-dimethylcyclohexylamine. The mixture was stirred at 0-5° C. for one hour and stirred at room temperature overnight. The mixture was washed first with 125 ml of slightly acidic water (pH 5) and then with 125 ml of water. The

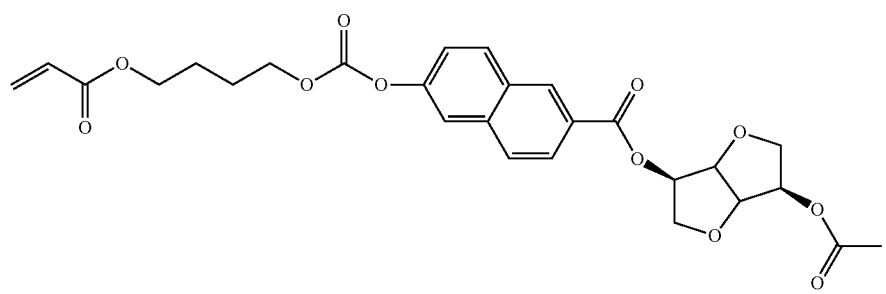

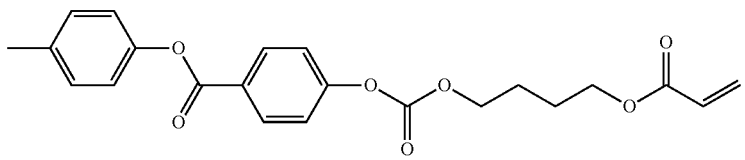

organic phase was dried over sodium sulfate and filtered through silica gel. The filtrate was precipitated with 100 ml of methanol. The resulting product was filtered off with suction and dried. 1.4 g (10%) of the desired compound were obtained.

HTP=32 μm$^{-1}$ 2.6) Preparation of a Mixture of the Compounds

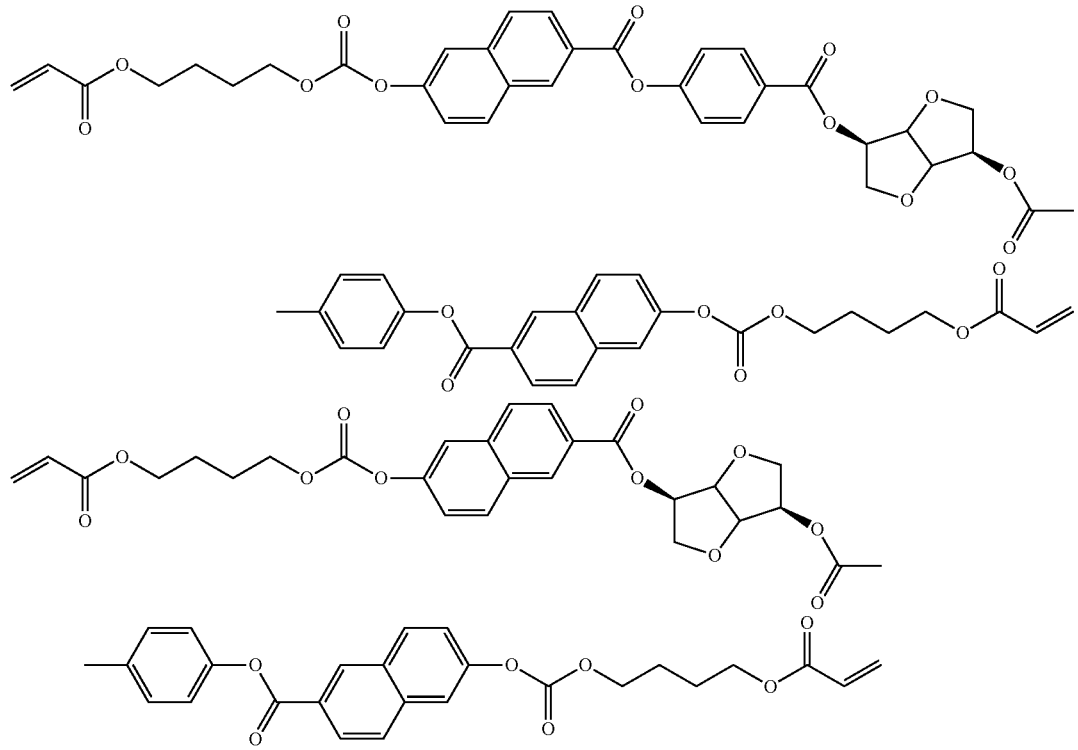

17.0 g (46 mmol) of 6-(4-acryloyloxybutoxycarbonyloxy)-2-naphthoic acid were stirred for one hour in 90 ml of oxalyl chloride with addition of 20 mg of Kerobit BHT and 9 drops of DMF. Subsequently, the excess oxalyl chloride was distilled off. The residue was dissolved in 90 ml of methylene chloride and added dropwise at 0-5° C. to a solution consisting of 3.9 g (10 mmol) of compound (2), 2.7 g (10 mmol) of compound (1), 11.5 g (90 mmol) of N,N-dimethylcyclohexylamine and 90 ml of methylene chloride, followed by stirring for 30 min at 0-5° C. and overnight at room temperature. The reaction mixture was then stirred at 40° C. for 5 hours, then filtered through silica gel and precipitated with 450 ml of methanol. The mixture was stirred at room temperature over the weekend. The resulting product was filtered off with suction. The purification was effected by dissolving in 100 ml of methylene chloride and reprecipitating with 200 ml of methanol. After two hours, the product was filtered off with suction, then stirred once again in water and filtered off with suction again. After drying at 40° C. under reduced pressure overnight, 9.1 g of the desired mixture were obtained.

HTP=30 μm$^{-1}$ 2.7) Preparation of the Compound

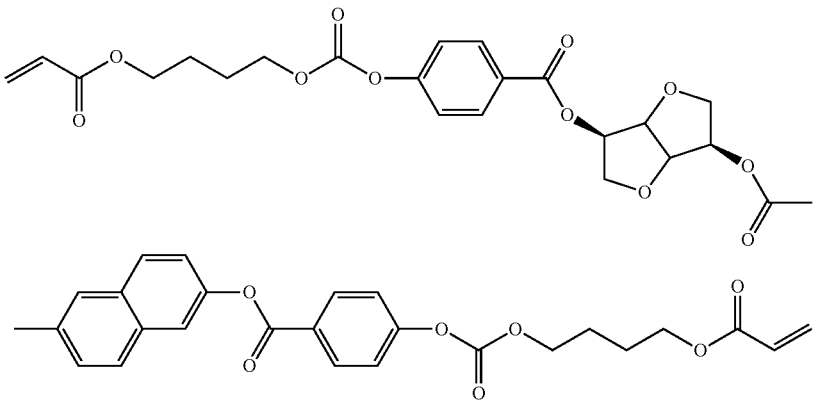

The synthesis was effected in two stages:
Stage 1:
2.9 g (9 mmol) of 4-(4-acryloyloxybutyloxycarbonyloxy)benzoic acid were stirred in 20 ml of oxalyl chloride with addition of 3 mg of Kerobit BHT and 2 drops of DMF for one hour. Subsequently, the excess oxalyl chloride was distilled off. The residue was dissolved in 26 ml of methylene chloride and added dropwise at 0-5° C. to a solution consisting of 3.2 g (10 mmol) of compound (3), 3.7 g (29 mmol) of N,N-dimethylcyclohexylamine and 26 ml of methylene chloride, and then stirred at 0-5° C. for 2 hours.
Stage 2:
5.8 g (18 mmol) of 4-(4-acryloyloxybutyloxycarbonyloxy)benzoic acid were stirred in 40 ml of oxalyl chloride with addition of 6 mg of Kerobit BHT and 4 drops of DMF for one hour. Subsequently, the excess oxalyl chloride was distilled off. The residue was dissolved in 52 ml of methylene chloride and added dropwise at 0-5° C. to the already prepared solution from stage 1, admixed with 7.7 g (60 mmol) of N,N-dimethylcyclohexylamine. The mixture was stirred at 0-5° C. for one hour and at room temperature overnight. Then the mixture was heated to 40° C. and stirred at this temperature for 5 hours. Subsequently, the mixture was washed first with 250 ml of slightly acidic water (pH 5) and then with 250 ml of water. The organic phase was dried over sodium sulfate and filtered through silica gel. The filtrate was partly concentrated and then precipitated with 150 ml of methanol. The product was stirred at room temperature for a further hour, then filtered off with suction and dried. 1.8 g (9%) of the desired compound were obtained.

HTP=31 µm$^{-1}$ 2.8) Preparation of the Compound

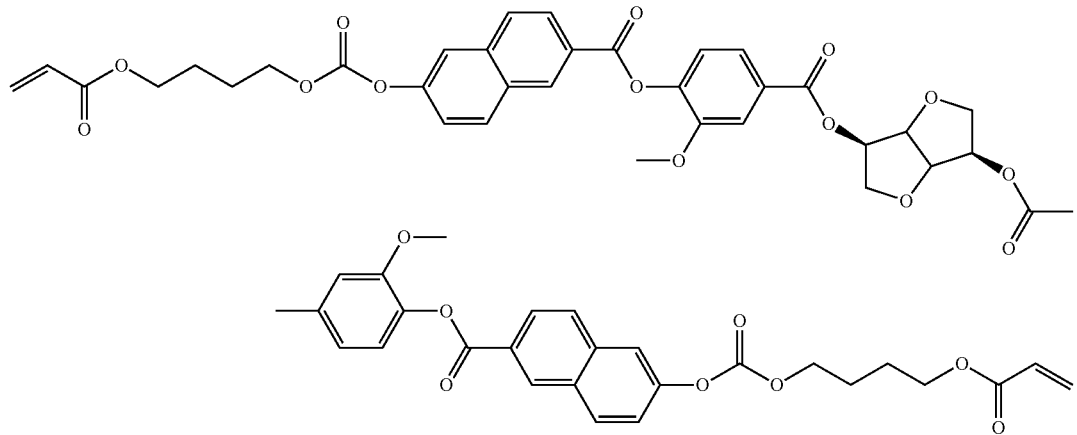

11.1 g (31 mmol) of 6-(4-acryloyloxybutoxycarbonyloxy)-2-naphthoic acid were stirred in 45 ml of oxalyl chloride with addition of 150 mg of hydroxy-TEMPO and 5 drops of TMF for one hour. Subsequently, the excess oxalyl chloride was distilled off. The residue was dissolved in 45 ml of methylene chloride and added dropwise at 0-5° C. to a solution consisting of 6.5 g (15 mmol) of compound (4), 4.9 g (39 mmol) of N,N-dimethylcyclohexylamine and 45 ml of methylene chloride. The mixture was stirred at 0-5° C. for 2 hours and then at room temperature overnight. Then the reaction mixture was stirred at 40° C. for 6 hours and at room temperature over the weekend. The solution was then washed first with 500 ml of acidic water (pH 3) and then with 500 ml of water. The organic phase was dried over 30 g of sodium sulfate and filtered. The filtrate was purified in concentrated form by means of column chromatography (SiO$_2$; 3:1 toluene/ethyl acetate).

2.9) Preparation of the Compound

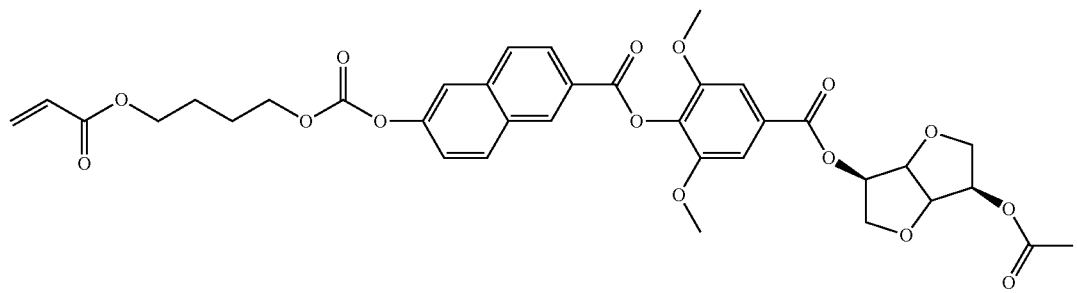

-continued

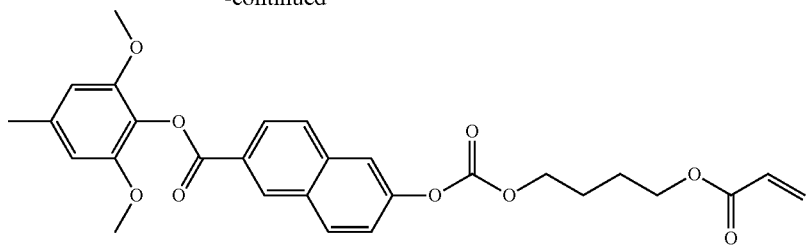

17.1 g (48 mmol) of 6-(4-acryloyloxybutoxycarbonyloxy)-2-naphthoic acid were stirred in 65 ml of oxalyl chloride with addition of 200 mg of hydroxy-TEMPO and 8 drops of DMF for one hour. Subsequently, the excess oxalyl chloride was distilled off. The residue was dissolved in 70 ml of methylene chloride and added dropwise at 0-5° C. to a solution consisting of 10.0 g (20 mmol) of compound (5), 7.7 g (61 mmol) of N,N-dimethylcyclohexylamine and 70 ml of methylene chloride. The mixture was stirred at 0-5° C. for 2 hours and at room temperature overnight. Then the reaction mixture was stirred at 40° C. for 6 hours. After cooling to room temperature, the solution was washed first with 500 ml of acidic water (pH 3) and then with 500 ml of water. The organic phase was dried over sodium sulfate and concentrated. The product was purified by means of column chromatography ($SiO_2$, 1:2 petroleum ether/ethyl acetate to 2:1 petroleum ether/ethyl acetate). 1.0 g (4%) of the desired compound was obtained.

HTP=19 μm$^{-1}$ 2.10) Preparation of the Compound

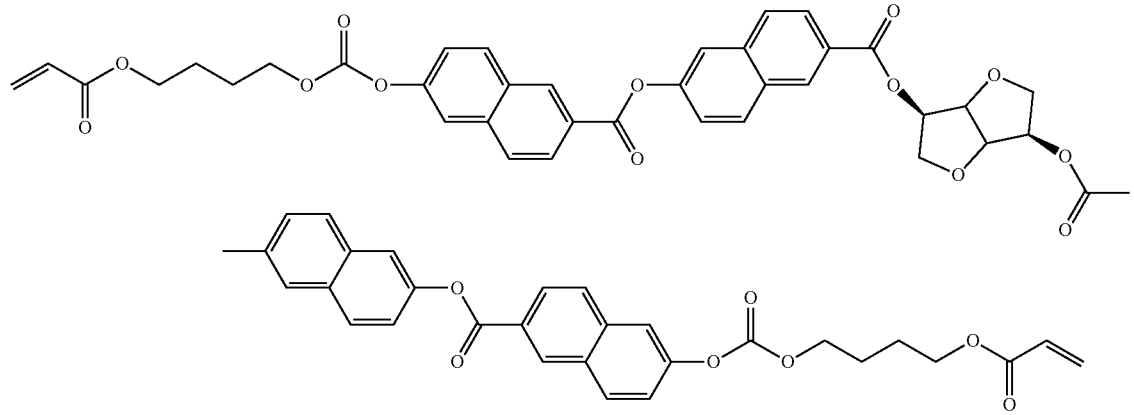

5.3 g (10 mmol) of compound (6) were stirred in 45 ml of oxalyl chloride with addition of 4 mg of Kerobit BHT and 4 drops of DMF for one hour. Subsequently, the excess oxalyl chloride was distilled off. The residue was added to 180 ml of methylene chloride and added dropwise at 0-5° C. to a solution consisting of 0.63 g (4.3 mmol) of isomannitol, 4.2 g (33 mmol) of N,N-dimethylcyclohexylamine and 20 ml of methylene chloride. The mixture was stirred at 0-5° C. for 30 min and at room temperature over the weekend. Then the reaction mixture was stirred at 40° C. for 5.5 hours. After cooling to room temperature, the solution was washed first with 200 ml of acidic water (pH 3) and then with 200 ml of water. The organic phase was dried over sodium sulfate, filtered and substantially concentrated. The remaining solution was precipitated with 200 ml of 1:1 methanol/water, filtered off with suction and dried. 1.3 g (26%) of the desired compound were obtained.

The invention claimed is:

1. A compound of the general formula I

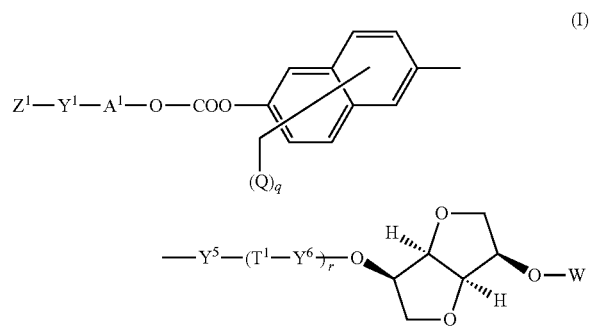
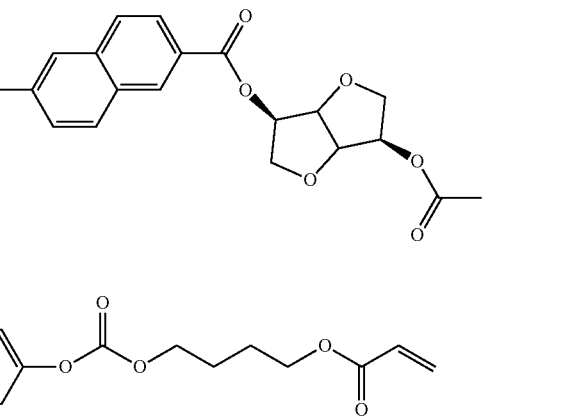

in which the variables are each defined as follows:

W is a $(Y^4\text{-}T^2\text{-})_s(Y^3\text{-}A^2\text{-})_tY^2\text{---}Z^2$ moiety, $Z^1$, $Z^2$ are each independently hydrogen, optionally substituted $C_1$-$C_{20}$-alkyl in which the carbon chain may be interrupted by oxygen atoms in ether function, sulfur atoms in thioether function or by nonadjacent imino or $C_1$-$C_4$-alkylimino groups, or reactive radicals through which polymerization can be brought about, $A^1$, $A^2$ are each independently spacers which have from 1 to 30 carbon atoms and in which the carbon chain may be interrupted by oxygen atoms in ether function, sulfur atoms in thioether function or by nonadjacent imino or $C_1$-$C_4$-alkylimino groups, $Y^1$, $Y^2$ are each independently a chemical single bond, oxygen, sulfur, —CO—, —O—CO—, —CO—O—, —S—CO—, —CO—S—, —NR—CO— or —CO—NR—, $Y^3$ when s>0:
  independently of $Y^1$ and $Y^2$ is as defined therefor or —O—COO—,
  when s=0:
  is a chemical single bond or —CO—,
$Y^4$ is a chemical single bond, oxygen, sulfur, —CO—, —O—CO—, —CO—O—, —S—CO—, —CO—S—, —NR—CO— or —CO—NR—, with the proviso that $Y^4$, when bonded to the oxygen atom of the isomannitol unit, is a chemical single bond or —CO—,
$Y^5$ when r=1:
  is a chemical single bond, oxygen, sulfur, —CO—, —O—CO—, —CO—O—, —S—CO—, —CO—S—, —NR—CO— or —CO—NR—,
  when r=0:
  is a chemical single bond or —CO—,
$Y^6$ is a chemical single bond or —CO—,
R is hydrogen or $C_1$-$C_4$-alkyl,
$T^1$, $T^2$ are each independently divalent saturated or unsaturated, optionally substituted and optionally fused iso- or heterocyclic radicals,
Q is halogen, $NO_2$, NO, CN, CHO, $L^1$, CO-$L^1$, $X^1$—CO-$L^1$, $X^1$—SO-$L^1$, $X^1$—$SO_2$-$L^1$, $X^1$-$L^{1\prime}$, CO—$X^1$-$L^{1\prime}$, O—CO—$X^1$-$L^{1\prime}$, SO—$X^1$-$L^{1\prime}$ or $SO_2$—$X^1$-$L^{1\prime}$, where
  $L^1$ is $C_1$-$C_{20}$-alkyl, $C_2$-$C_{20}$-alkenyl, $C_2$-$C_{20}$-alkynyl, $C_6$-$C_{10}$-aryl, heteroaryl having from 2 to 12 carbon atoms, $C_6$-$C_{10}$-aryl-$C_1$-$C_{20}$-alkyl, $C_6$-$C_{10}$-aryl-$C_2$-$C_{20}$-alkenyl, $C_6$-$C_{10}$-aryl-$C_2$-$C_{20}$-alkynyl, heteroaryl-$C_1$-$C_{20}$-alkyl, heteroaryl-$C_1$-$C_{20}$-alkenyl or heteroaryl-$C_1$-$C_{20}$-alkynyl having in each case from 2 to 12 carbon atoms in the heteroaryl radical, where the $C_1$-$C_{20}$ carbon chain may be interrupted by oxygen atoms in ether function, sulfur atoms in thioether function, nonadjacent imino, $C_1$-$C_{20}$-alkylimino and/or carbonyl groups, and both the $C_6$-$C_{10}$-aryl and the heteroaryl may be substituted by one or more substituents selected from the group consisting of halogen, $NO_2$, NO, CN, CHO, $L^2$, CO-$L^2$, $X^2$—CO-$L^2$, $X^2$—SO-$L^2$, $X^2$—$SO_2$-$L^2$, $X^2$-$L^{2\prime}$, CO—$X^2$-$L^{2\prime}$, O—CO—$X^2$-$L^{2\prime}$, SO—$X^2$-$L^{2\prime}$ and $SO_2$—$X^2$-$L^{2\prime}$,
  $L^{1\prime}$ is hydrogen or independently of $L^1$ is as defined for $L^1$,
  $L^2$ is $C_1$-$C_{20}$-alkyl, $C_2$-$C_{20}$-alkenyl, $C_2$-$C_{20}$-alkynyl, $C_6$-$C_{10}$-aryl, heteroaryl having from 2 to 12 carbon atoms, $C_6$-$C_{10}$-aryl-$C_1$-$C_{20}$-alkyl, $C_6$-$C_{10}$-aryl-$C_2$-$C_{20}$-alkenyl, $C_6$-$C_{10}$-aryl-$C_2$-$C_{20}$-alkynyl, heteroaryl-$C_1$-$C_{20}$-alkyl, heteroaryl-$C_2$-$C_{20}$-alkenyl or heteroaryl-$C_2$-$C_{20}$-alkynyl having in each case from 2 to 12 carbon atoms in the heteroaryl radical,
  $L^{2\prime}$ is hydrogen or independently of $L^2$ is as defined for $L^2$
and
$X^1$, $X^2$ are each independently oxygen, sulfur or $NL^{1\prime}$ or $NL^{2\prime}$,
r, t are each independently 0 or 1,
s is 0, 1, 2 or 3,
  where the particular variables $T^2$ and $Y^4$, in the case that s>1, may be the same as one another or different than one another,
and
q is 0, 1, 2, 3 or 4.

2. A compound according to claim 1, in which the variables $T^1$ and $T^2$ are each independently

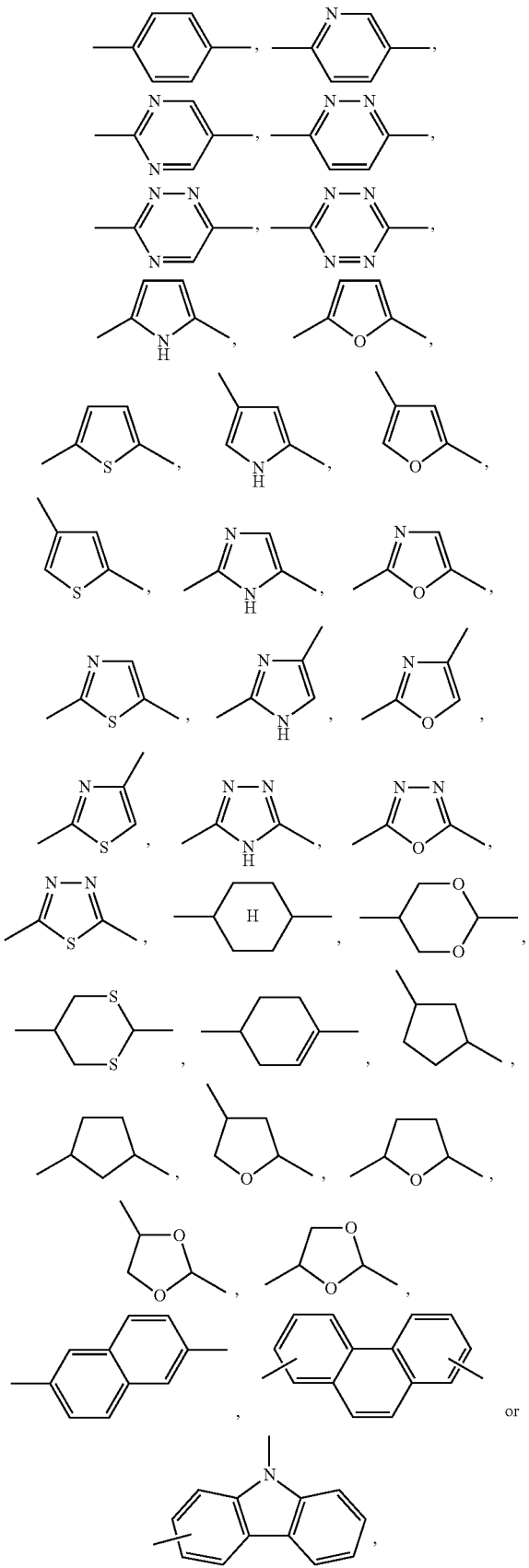

where the radicals

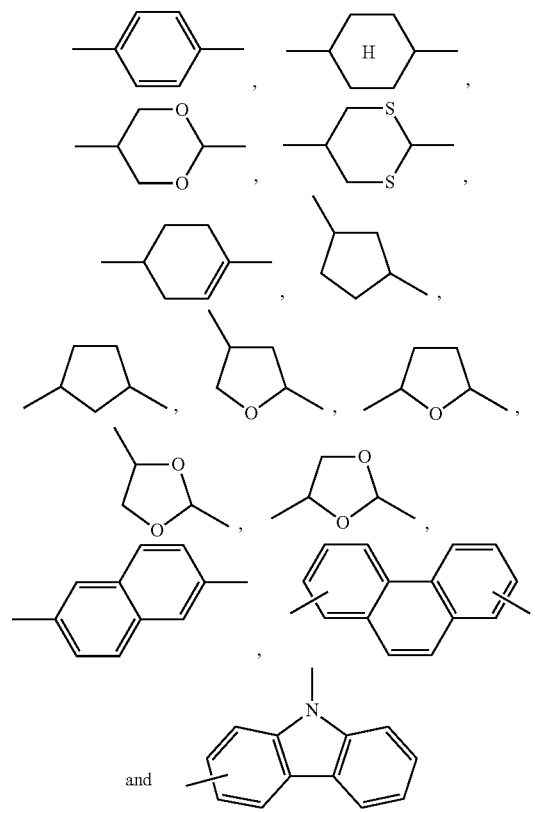

and

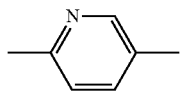

—irrespective of the specific selection of the Q substituents of the 2,6-naphthyl radical in formula I of claim 1—may be substituted by up to four (q equal to 0, 1, 2, 3 or 4) identical or different Q substituents of the general definition according to claim 1,
the radical

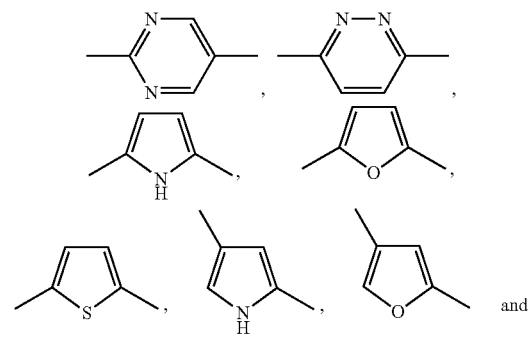

—irrespective of the specific selection of the Q substituents of the 2,6-naphthyl radical in formula I of claim 1—may be substituted by up to three (q equal to 0, 1, 2 or 3) identical or different Q substituents of the general definition according to claim 1, the radicals

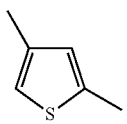

—irrespective of the specific selection of the Q substituents of the 2,6-naphthyl radical in formula I of claim 1—may be substituted by up to two (q equal to 0, 1 or 2) identical or different Q substituents of the general definition according to claim 1, and the radicals

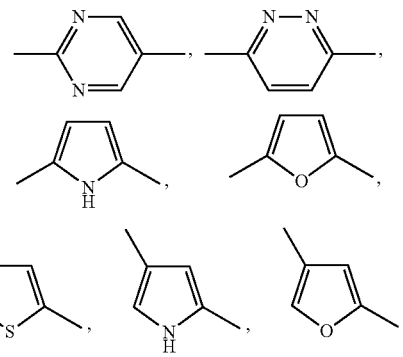

—irrespective of the specific selection of the Q substituents of the 2,6-naphthyl radical in formula I of claim 1—may be substituted by up to one (q equal to 0 or 1) Q substituent of the general definition according to claim 1.

3. A compound according to claim 1 in which the variables $T^1$ and $T^2$ are each independently

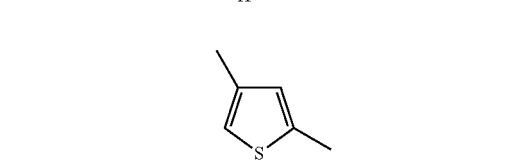

where the radicals—irrespective of the specific selection of the Q substituents of the 2,6-naphthyl radical in formula I of claim 1—may be substituted by up to four (q equal to 0, 1, 2, 3 or 4) identical or different Q substituents of the general definition according to claim 1.

4. A compound according to claim 1, in which $(Y^4\text{-}T^2\text{-})_s$ in the variable W of the formula I corresponds to a moiety of the formula Ia

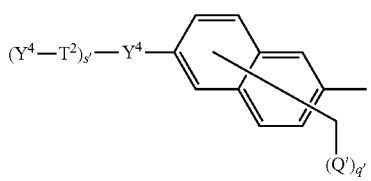

(Ia)

in which:

Q'—irrespective of the specific selection of the Q substituents of the 2,6-naphthyl radical in formula I of claim 1—is identical or different substituents of the general definition Q according to claim 1, q' is 0, 1, 2, 3 or 4 and s' is 0, 1 or 2, where the variables $Y^4$ and $T^2$ possess the same definition as in the preceding claims and the variables $Y^4$ when s'>0 and the variables $T^2$ when s'>1 may be the same as one another or different than one another.

5. A compound according to claim 1, in which t is 1 and $Y^3$ corresponds to an —O—COO— group.

6. A compound according to claim 1, in which at least one of the $Z^1$ and $Z^2$ radicals is a reactive radical.

7. A compound according to claim 1, in which at least one of the $Z^1$ and $Z^2$ radicals is a reactive radical

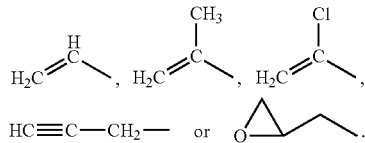

8. A compound according to claim 1, in which at least one of the $Z^1$ and $Z^2$ radicals is a reactive radical

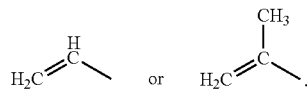

9. A compound according to claim 1, in which t is 1 and the $Z^1$—$Y^1$-$A^1$- and -$A^2$-$Y^2$—$Z^2$ moieties are the same.

10. A compound according to claim 1, in which $Z^1$—$Y^1$ and $Z^2$—$Y^2$ are identical reactive moieties

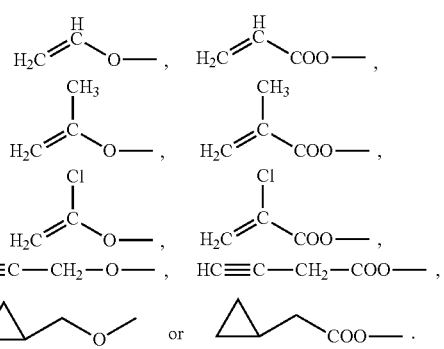

11. A compound according to claim 1, in which $Z^1$—$Y^1$ and $Z^2$—$Y^2$ are identical reactive moieties

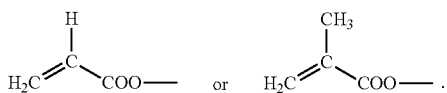

12. A liquid-crystalline composition comprising at least one compound of the formula I according to claim 1.

13. A method of chiral doping comprising adding the compounds of the formula I according to claim 1 to a composition.

* * * * *